(12) United States Patent
Arora et al.

(10) Patent No.: US 7,601,368 B2
(45) Date of Patent: Oct. 13, 2009

(54) PURIFIED ARABINOGALACTAN-PROTEIN (AGP) COMPOSITION USEFUL IN THE TREATMENT PSORIASIS AND OTHER DISORDERS

(75) Inventors: Sudershan Kumar Arora, Maharashtra (IN); Vandita Srivastava, Maharashtra (IN); Sameer Shankar Walunj, Maharashtra (IN)

(73) Assignee: Lupin Limited, Maharashtra (IN)

( * ) Notice: Subject to any disclaimer, the term of this patent is extended or adjusted under 35 U.S.C. 154(b) by 286 days.

(21) Appl. No.: 10/931,814

(22) Filed: Sep. 1, 2004

(65) Prior Publication Data

US 2006/0045930 A1    Mar. 2, 2006

(51) Int. Cl.
*A61K 36/00* (2006.01)
(52) U.S. Cl. .................. 424/725; 424/774; 424/779; 514/1; 514/8
(58) Field of Classification Search .................. 424/725, 424/724; 514/8, 1
See application file for complete search history.

(56) References Cited

U.S. PATENT DOCUMENTS

2003/0194456 A1    10/2003    Arora et al.

FOREIGN PATENT DOCUMENTS

WO    01/00682 A1    1/2001

OTHER PUBLICATIONS

Wikipedia Online Encyclopedia: Argemone Mexicana; URL: <http://en.wikipedia.org/wiki/Argemone_mexicana> accessed May 30, 2007, one page.*
Sukumar et al. Studies on the Leaves of Argemone Mexicana; Fitoterapia, vol. IV, No. 6, 1984, pp. 352-353.*
Showalter, Am: Aribinogalactan-Proteins: Structure, Expression and Function; Cell. Mol. Life. Sci. 58 (2001) 1399-1417.*
Kristian Reich et al. The Journal of Investigative Dermatology, Feb. 2 2001, 116:319-329.
G.B. Hawes, et al. "Extracellular Arabinogalactan From Suspension-Cultured Red Kindney Bean Root Cells" Phytochemistry, 1972, vol. 11, pp. 1461-1465.
Ashcroft, et al. "Systematic review of comparative eficacy and tolerability of calcipotriol in treating chronic plaque psoriasis" BMJ, 2000, 320, 963-967.
Robert S. Stern, et al. "The Carcinogenic Risk of Treatments for Severe Psoriasis" Cancer, Jun. 1, 1994, 73, 2759-2764.
R.L. Anderson, et al. "A Carbohydrate=-binding Arabinogalactan-Protein from Liquid Suspension Cultures of Endosperm from *Lolium multiflorum*" Aust. J. Plant Physiol., (1977), 4:143-58.
Raychaudhuri, et al., International Journal of Immunopharmacology 1999, 21; 609-615.

(Continued)

*Primary Examiner*—Patricia Leith
(74) *Attorney, Agent, or Firm*—Ladas and Parry LLP

(57) ABSTRACT

A purified Arabinogalactan-Protein (AGP) composition isolated through a selective method from the leaves and/or stems of *Argemone mexicana* plant is described. Also described is a purified Arabinogalactan-Protein (AGP) composition isolated from the leaves and/or stems of *Argemone mexicana* plant, which has one or more of the following effects: immunosuppression, lymphoproliferation inhibition, cytokine modulation such as IL-2 inhibition, IFN-γ inhibition, or IL-10 induction; keratinocyte proliferation inhibition, keratolytic activity and inhibitory activity in Mouse Ear Swelling test (MEST).

20 Claims, 12 Drawing Sheets

The Selective Method for Isolation of Purified Arabinogalactan-Protein (AGP) Composition as per the Present Invention

OTHER PUBLICATIONS

Krueger, et al. J Am. Aca. Dermatol. Aug. 2000, 43:281-285.
Classen, B. et al. Carbohydrate Research 327:497-504 (2000).
Fortune, et al. J. of American Academy of Dermatology 39(2) (Part 1):196-201 (1998).
Brynskov, et al. Gut, 1990, 31, 795-799.
Cornacoff, J.B., et al., Fundamental and Applied Toxicology, 1992, 19(1): 157-158.
Cornacoff, et al., Fundamental and Applied Toxicology, 1988, 10:40-44.
British National Formulary, Mar. 2000, No. 41; 522-529.
Merkle, R.K. et al. Methods in Enzymology, 1994, 230:1-15.
York, W.S., et al, Method in Enzymology, 1985, 118:3-40.
Birgit Classen, et al. "Characterization of an Arabinogalactan-Protein Isolated from Pressed Juice of Echinacea purpurea by Precipitation with the β-Glucosyl Yariv Reagent" Carbohydrate Research (327 (2000) 497-504).
Donal G. Fortune, et al. "What Patients with Psoriasis Believe About Their Condition", Journal of The American Academy of Dermatology, vol. 39, No. 2, Part 1((1998) pp. 196-201)).
G. Seifert et al. Annu. Rev. Plant Biol. 2007, 58, p. 137 abstract, CMLS 2001, 58, pp. 138-161.
C.J. Schultz, et al. Plant Physiology 2002, 129, pp. 1448-1463.
GMP for Botanicals, Business Horizons, 2003, p. 9 (ed. P.K. Mukherjee, et al.).
Natural Products Isolation, Humana Press, 1988, pp. 344-347 (ed. R. Cannell et al.).
Burley Curing Technology, Univ. of. Kentucky, 2004, pp. 1-6.
Showalter A.M. "Arabinogalactan-proteins: structure, expression and function" CMLS, Cell. Mol. Life Sciences 58(2001) pp. 1399-1417.
Schnippr, L. et al. "The New England Journal of Medicine" 2001 vol. 345, No. 4, pp. 284-287.
Menter, A. et al. "Current and future management of psoriasis" The Lancet, 2007 vol. 370 pp. 272-284.
Lowes, M. et al. "Pathogenesis and therapy of psoriasis" Nature 2007 vol. 445 pp. 866-873.

* cited by examiner

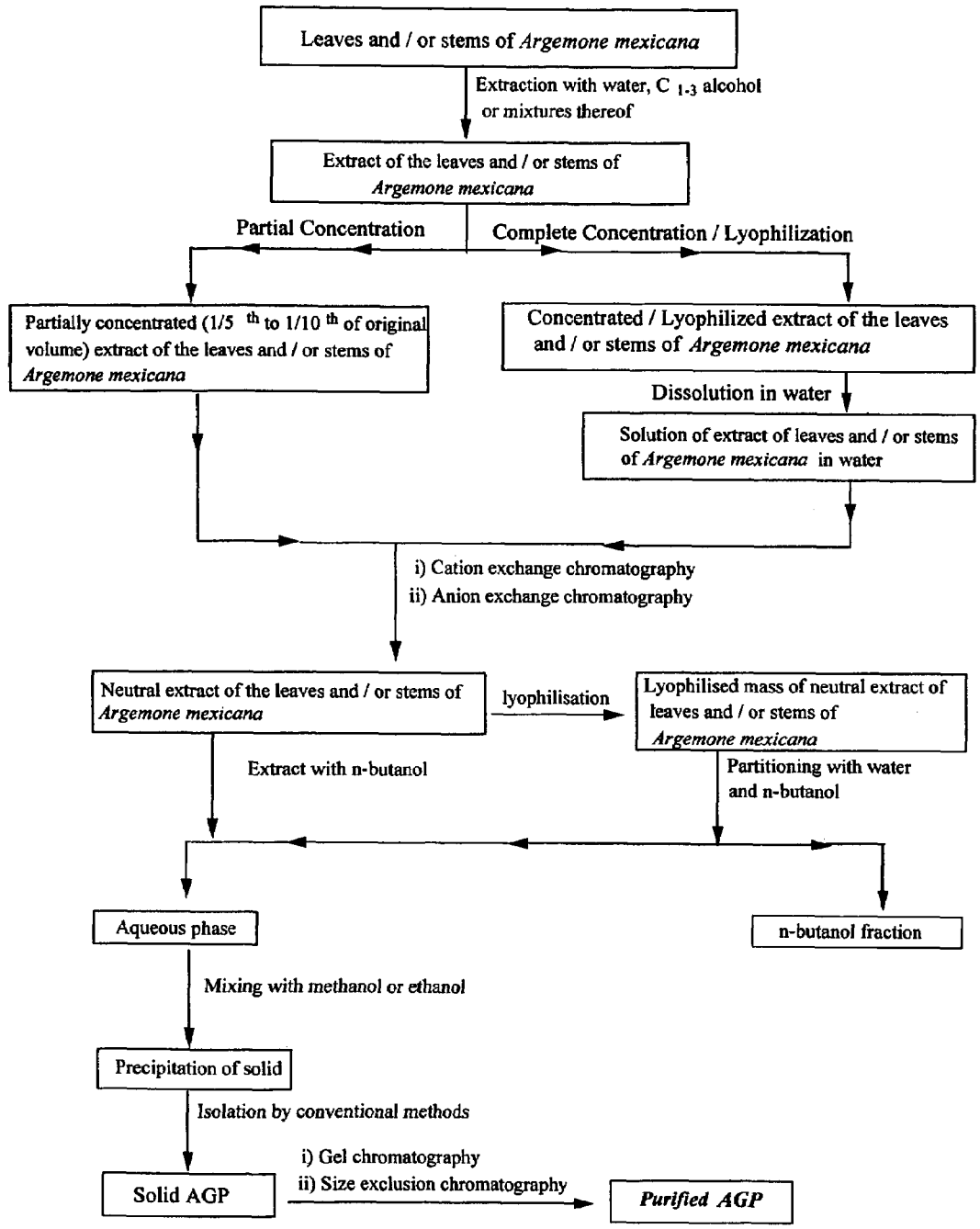
Fig. 1 : The Selective Method for Isolation of Purified Arabinogalactan-Protein (AGP) Composition as per the Present Invention

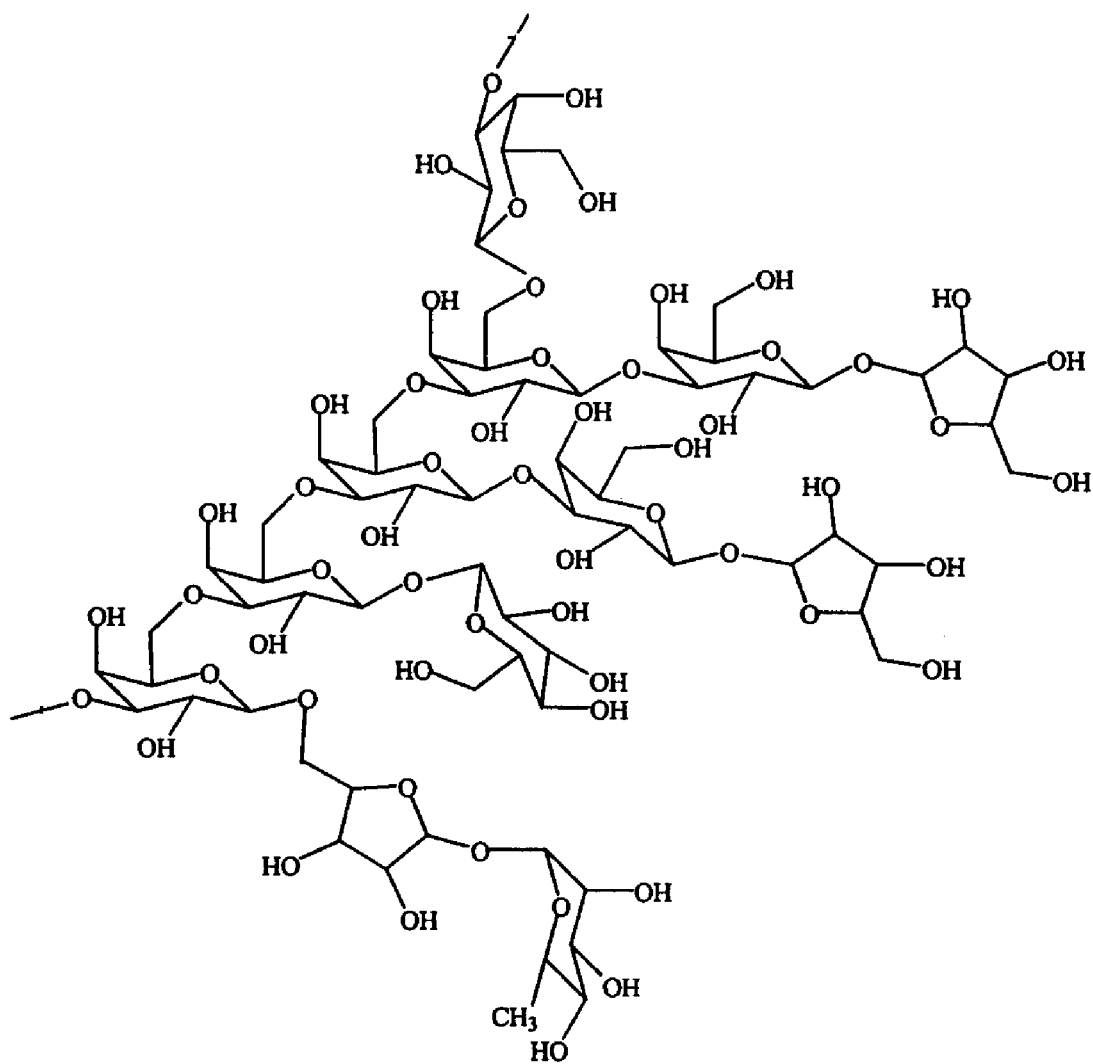
Fig. 2 : Proposed Structure of AGP Composition

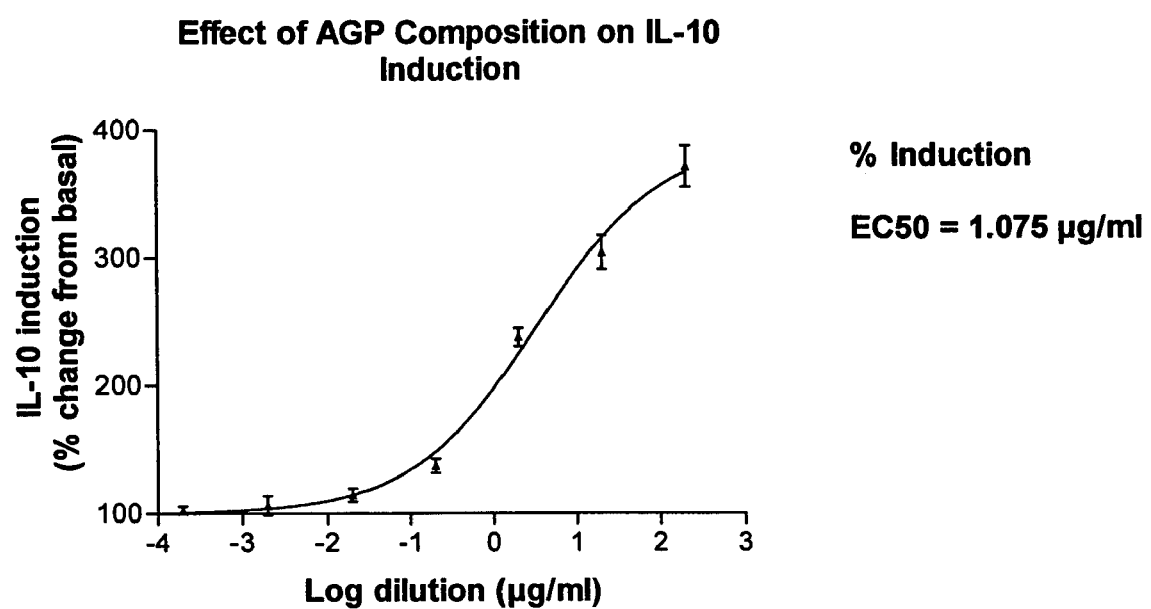
Fig. 3 : Effect of AGP Composition on IL 10 Induction

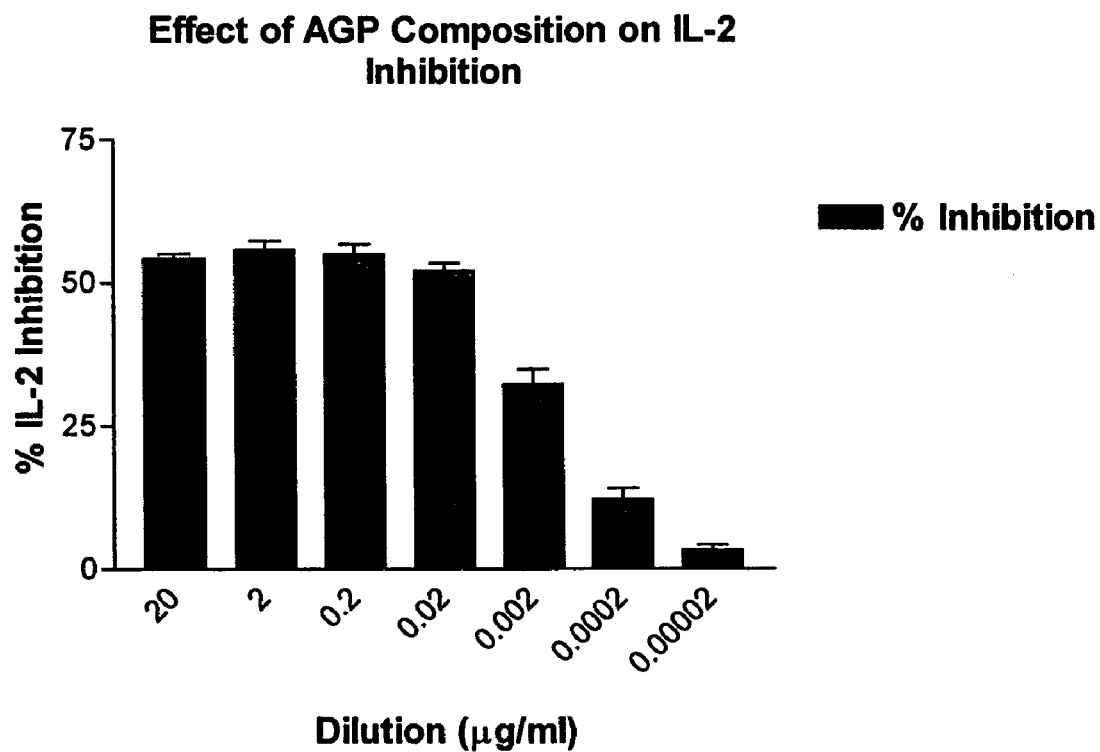
Fig. 4 : Effect of AGP Composition on Percent IL-2 Inhibition

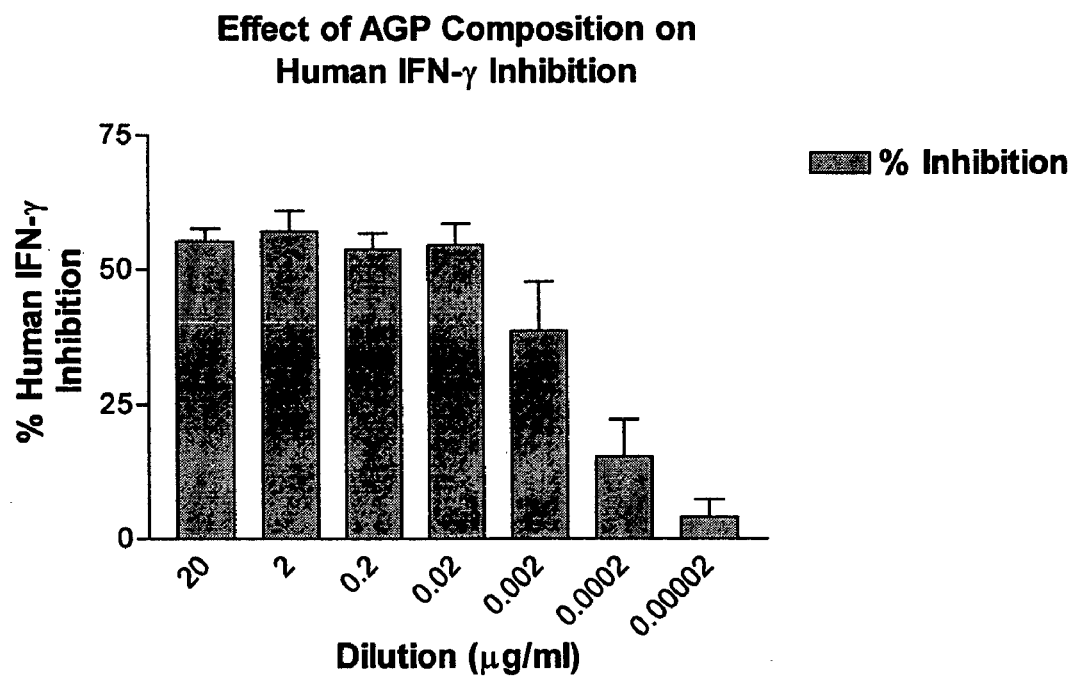
Fig. 5 : Effect of AGP Composition on Percent IFN-γ Inhibition

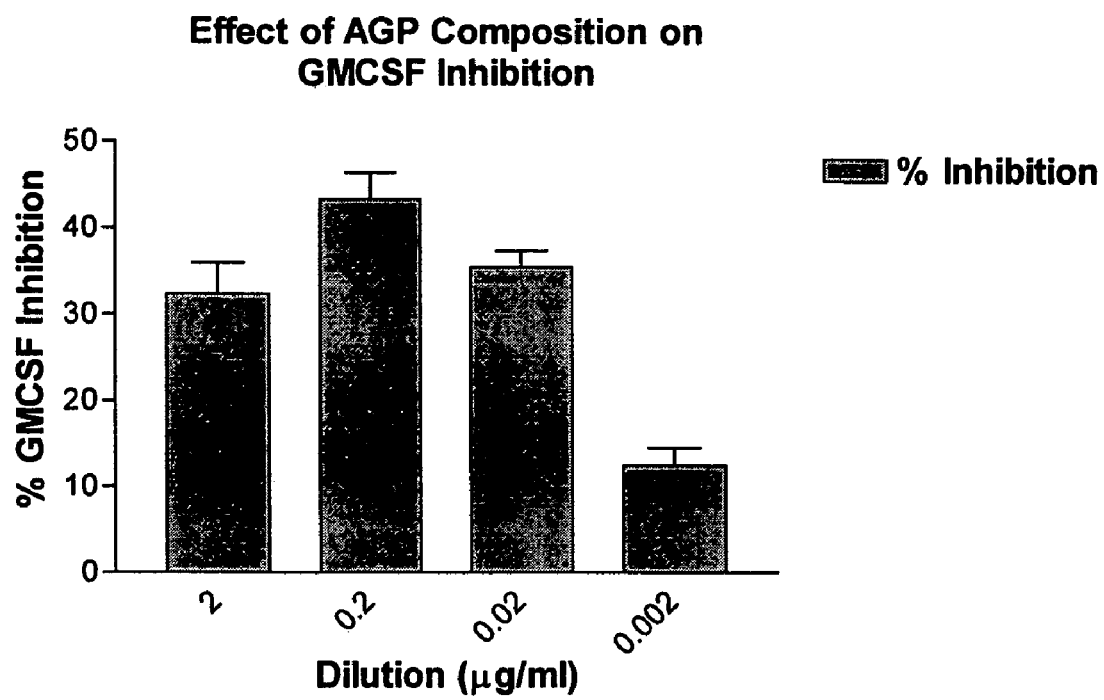
Fig. 6 : Effect of AGP Composition on Inhibition of GMCSF

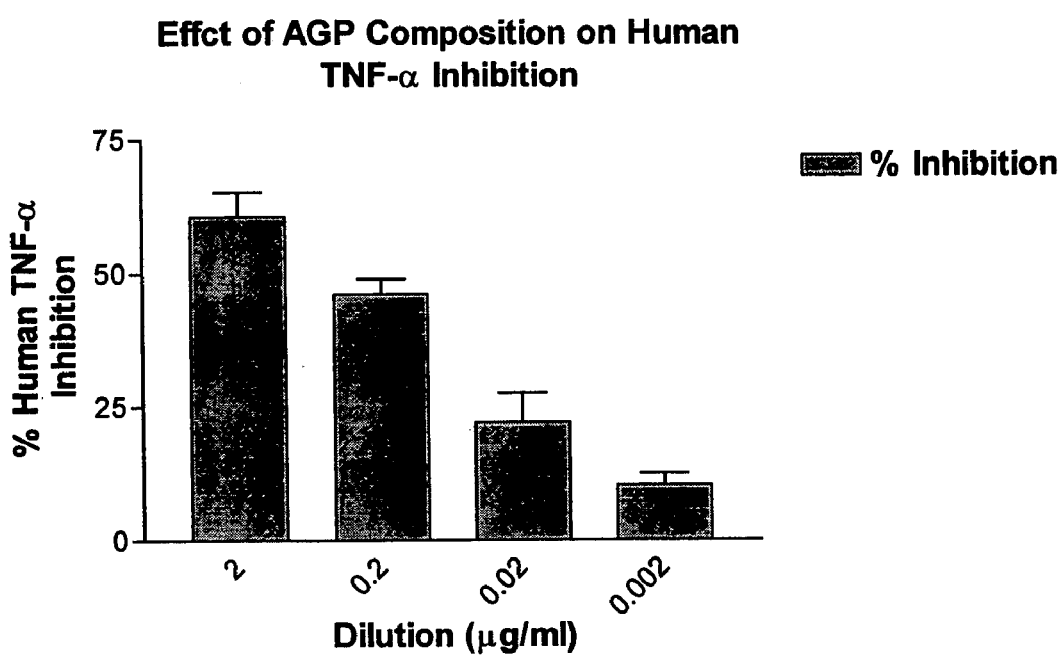
Fig. 7 : Effect of AGP Composition on Inhibition of Human TNF-α

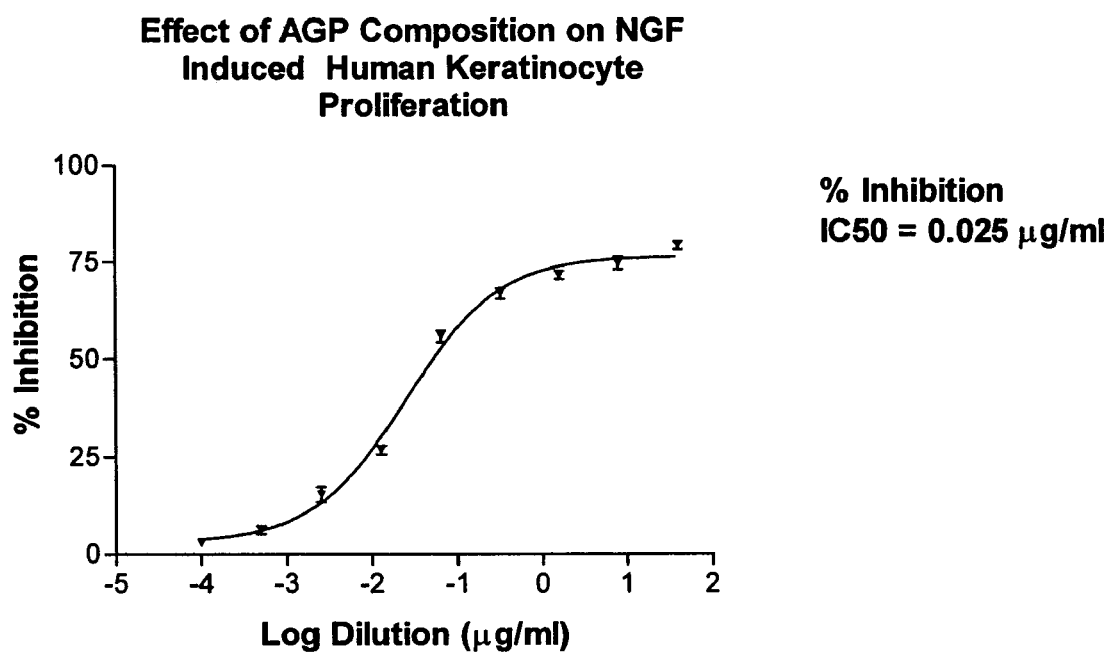
Fig. 8 : Effect of AGP Composition on NGF Induced Human Keratinocyte Proliferation

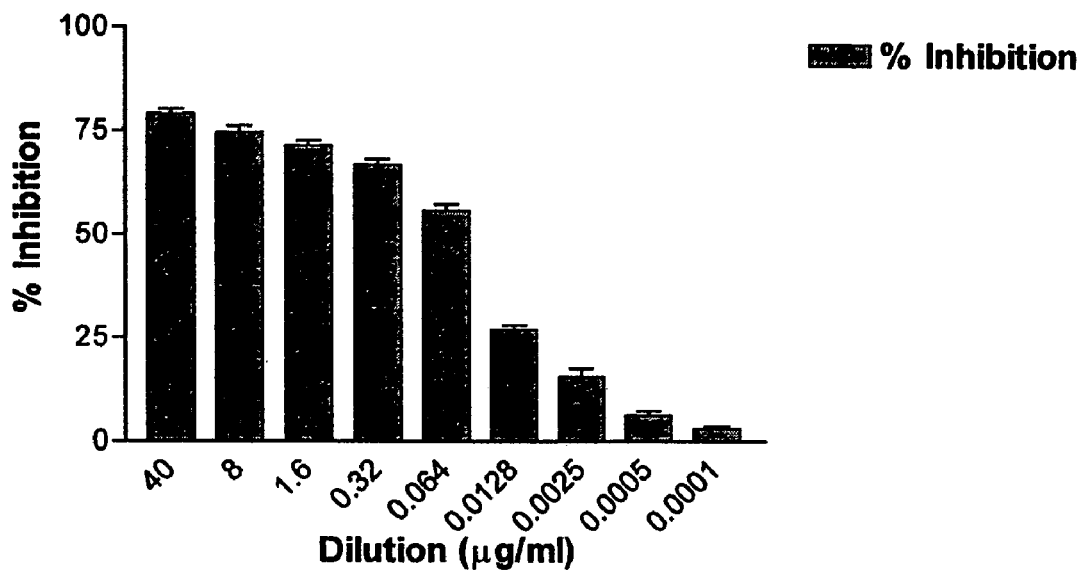
Fig. 9 : Effect of AGP Composition on NGF Induced Human Keratinocyte Proliferation

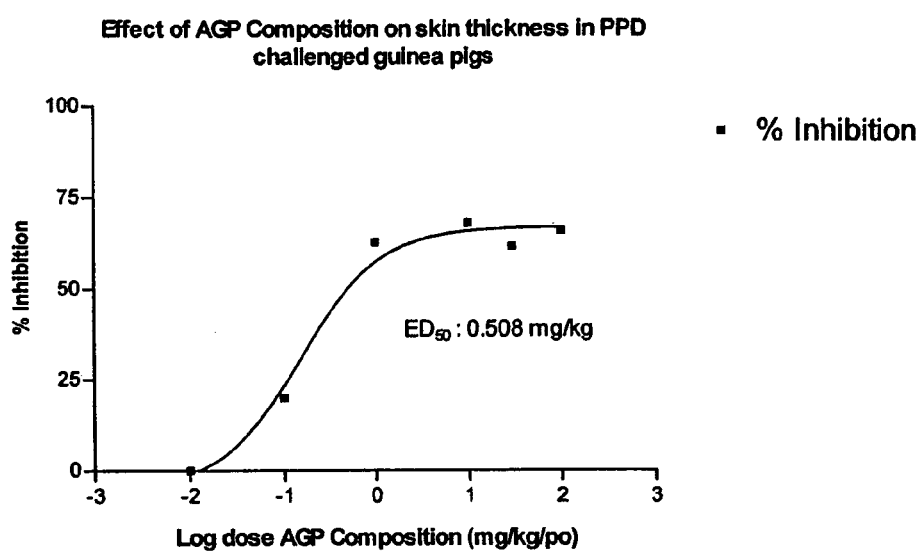
Fig. 10 : Effect of AGP Composition on Skin Thickness in PPD Challenged Guinea pigs

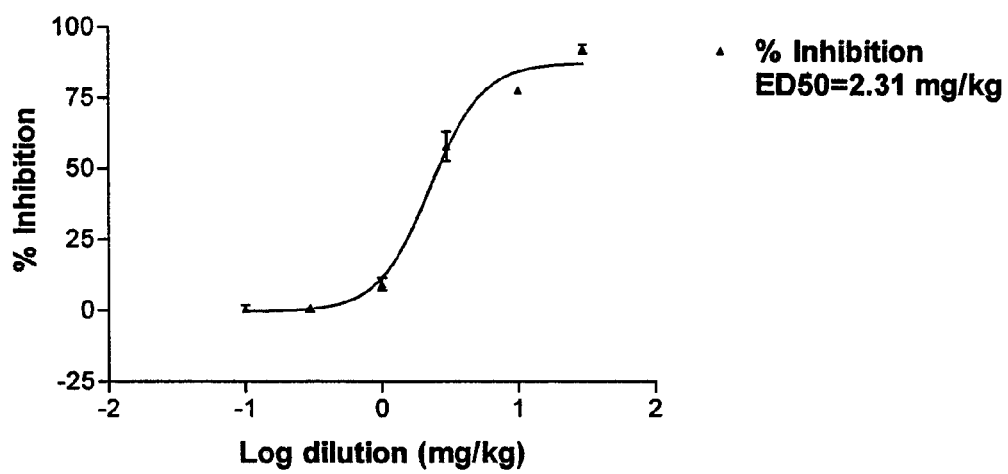
Fig. 11 : Effect of AGP Composition on Inhibition of Epidermal Thickness induced by TPA in Balb/c mice

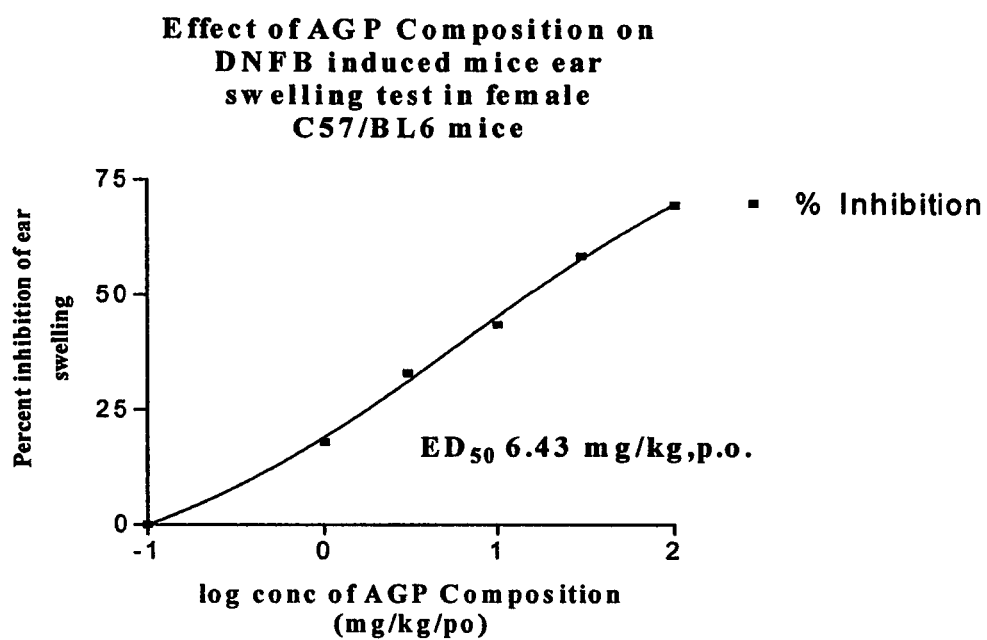
Fig. 12 : Effect of AGP Composition on DNFB Induced Mice Ear Swelling Test in Female C 57/BL 6 Mice

PURIFIED ARABINOGALACTAN-PROTEIN (AGP) COMPOSITION USEFUL IN THE TREATMENT PSORIASIS AND OTHER DISORDERS

FIELD OF THE INVENTION

The present invention relates to a purified Arabinogalactan-Protein (AGP) composition isolated through a selective method from the leaves and/or stems of *Argemone mexicana* plant.

The present invention also relates to a purified Arabinogalactan-Protein (AGP) composition isolated from the leaves and/or stems of *Argemone mexicana* plant, which has one or more of the following effects: immunosuppression, lymphoproliferation inhibition, cytokine modulation such as IL-2 inhibition, IFN-γ inhibition, or IL-10 induction; keratinocyte proliferation inhibition, keratolytic activity and inhibitory activity in Mouse Ear Swelling test (MEST).

DESCRIPTION OF THE ABBREVIATIONS/NOTATIONS USED HEREIN

Arabinogalactan-Protein: AGP
High Molecular Weight Arabinogalactan-Protein: AGP-HM
Low Molecular Weight Arabinogalactan-Protein: AGP-LM

BRIEF DESCRIPTION OF THE FIGURES

FIG. 1. is a chart summarizing the selective process for isolating purified AGP composition.

FIG. 2: shows the proposed structure of AGP composition.

FIG. 3: shows the effect of AGP composition on IL-10 Induction.

FIG. 4: shows the effect of AGP composition on Percent IL-2 Inhibition.

FIG. 5: shows the effect of AGP composition on Percent IFNγ Inhibition.

FIG. 6: shows the effect of AGP composition on Inhibition of GMCSF.

FIG. 7: shows the effect of AGP composition on Inhibition of human TNFα.

FIG. 8: shows effect of AGP composition on NGF Induced Human Keratinocyte Proliferation.

FIG. 9: shows effect of AGP composition on NGF Induced Human Keratinocyte Proliferation.

FIG. 10: shows effect of AGP composition on Skin Thickness in PPD challenged guinea pigs.

FIG. 11: shows effect of AGP Composition on Inhibition of Epidermal Thickness Induced by TPA (12-O-tetradecanoylphorbol-13-acetate) in Balb/c mice.

FIG. 12: shows the effect of AGP Composition on DNFB Induced Mice Ear Swelling Test in Female C 57/BL 6 Mice.

BACKGROUND OF THE INVENTION

Psoriasis is a skin disorder characterized by inflammatory and abnormal epidermal keratinocyte hyper-proliferation resulting in hyperplasia, thickening of the epidermis and the presence of red scale plaques. The chronic skin condition is recognized for its peculiar clinical symptoms, characterized by circumscribed red patches covered with white scales that result in itchy, flaky skin. Psoriasis is a very visible disease and frequently affects the face, scalp, trunk and limbs. The lesions in this chronic disease typically are subject to remission and excerbations.

Although, psoriasis manifests as a skin disorder, while not being bound to any theory, it is believed to be a disease of impaired or defective cell mediated immunity. Since the clinical appearance of psoriasis is largely caused by epidermal changes, the disease has traditionally been considered one of excessive keratinocyte proliferation and abnormal differentiation. Current evidence suggests that epidermal changes in psoriasis are caused by actions of T lymphocytes in skin lesions and that T lymphocytes induce or sustain the disease process. Psoriasis is portrayed as an autoimmune disease, where activated T-lymphocytes, producing multiple cytokines cause secondary epithelial abnormalities. Dysregulated lymphocytes produce cytokines that stimulate the proliferation of apoptosis-resistant keratinocytes. Psoriatic skin lesions are characterized by inflammation, with T cells and neutrophils infiltrating both the dermis and epidermis and excessive scaling related to epidermal hyperproliferation and aberrant keratinocyte differentiation [Reich K., Garbe C., Blaschke V., Maurer C., Middel P., Westhal G., Lippert U., and Neumann C., *J. Invest. Dermatol.*, 2001, 116, 319].

Autoimmune disorders are diseases caused by the body producing an immune response against its own tissues. The cause of autoimmune diseases is unknown, but it appears that there is an inherited predisposition in many cases in the development of an autoimmune disease.

In a few types of autoimmune disease (such as rheumatic fever), a bacteria or virus triggers an immune response, and the antibodies or T-cells attack normal cells because they have some part of their structure that resembles a part of the structure of the infecting germ.

Autoimmune disorders fall into two general types: those that damage many organs (systemic autoimmune diseases), and those where only a single organ or tissue is directly damaged by the autoimmune process (localized). Some of the most common types of autoimmune disorders are summarized in below:

| Systemic Autoimmune Diseases | Localized Autoimmune Diseases |
|---|---|
| Rheumatoid arthritis (joints; less commonly lung, skin) | Type 1 Diabetes Mellitus (pancreas islets) |
| Lupus [Systemic Lupus Erythematosus] (skin, joints, kidneys, heart, brain, red blood cells, other) | Hashimoto's thyroiditis, Graves' disease (thyroid) |
| Scleroderma (skin, intestine, less commonly lung) | Celiac disease, Crohn's disease, Ulcerative colitis (GI tract) |
| Sjogren's syndrome (salivary glands, tear glands, joints) | Multiple sclerosis*, Guillain-Barre syndrome (brain) |
| Goodpasture's syndrome (lungs, kidneys) | Addison's disease (adrenal) |
| Wegener's granulomatosis (sinuses, lungs, kidneys) | Primary biliary sclerosis, Sclerosing cholangitis, Autoimmune hepatitis (liver) |

The inflammatory process involves a series of events that can be elicited by numerous stimuli (e.g. infectious agents, ischemia, antigen-antibody interactions, and thermal or other physical injury). Each type of stimulus provokes a characteristic pattern of response that represents a relatively minor variation on a theme. At a macroscopic level, the response usually is accompanied by the familiar clinical signs of erythema, edema, tenderness and pain.

The symptoms observed in psoriatic patients include hyperplasia and abnormal cornification of epidermal cells ascribed to the excess turnover of the cells by hyper metabolism, asthenia of inflammatory response in the epidermal layer, vasodilation and leukocyte migration and infiltration into the epidermal cell layers. However, it is now recognized that epidermal hyperplasia is a reaction to the activation of immune system in focal skin regions, which in turn, is mediated by CD8+ and CD4+ T lymphocytes that accumulate in the diseased skin. Indeed, psoriasis is now recognized as the most prevalent T cell-mediated inflammatory disease of humans. The symptoms in psoriasis thus appear to be overly rapid growth of keratinocytes and shedding of scales from the skin surface. Within psoriatic lesions, the keratinocyte cell cycle time is reduced approximately 8 fold (36 vs. 311 hours in normal skin) and the number of dividing cell is doubled, resulting in a hyperplastic epidermis. Drug therapy is directed at slowing down this process.

It was found that PUVA therapy depleted lymphocytes in concert with disease improvements. These data are consistent with a role for T cells in pathogenesis. Cyclosporine, a known immunosuppressant was found to have dramatic effects on disease activity. Since cyclosporine has a major inhibitory effect on T cell activation, arguments began to be made that psoriasis was fundamentally an inflammatory disease.

T-lymphocytes must infiltrate the dermis and then adhere to keratinocytes to produce psoriatic plaque. Hence molecular regulating T cell adhesion and trafficking become tenable therapeutic targets and its role in pathophysiology is of considerable importance. Intravascular adhesion events can be inhibited by blocking chemokine triggering or blocking integrin binding (LFA-1 to ICAM-1). Integrin blockade or reduction of its surface expression could be an important event for lymphocytes trafficking which aid in anti-psoriatic therapy.

Immunosuppression, lymphoproliferation inhibition, cytokine modulation such as IL-2 inhibition, IFN-γ inhibition, or IL-10 induction; keratinocyte proliferation inhibition, keratolytic activity and inhibitory activity in MEST are known to be involved in anti-psoriatic activity.

The number of different and sometimes toxic treatments employed for amelioration of psoriasis is testimony to the resistant nature of this disease. As the majority (90%) of psoriasis patients have limited forms of the disease, topical treatments that include dithranol, tar preparations, corticosteroids and the recently introduced vitamin D3 analogues (calcipotriol, calcitriol) can be used. A minority (10%) of psoriasis patients have a more serious condition, for which a number of systemic therapeutic modalities are available. Specific systemic therapies include UVB, PUVA, methotrexate, vitamin A derivatives (acitretin) and immuno-suppressants such as cyclosporin A. The effectiveness of cyclosporin and FK-506 for treating psoriasis provides support for the T cell hypothesis as the prime cause of the disease.

The topical use of corticosteroids reduces the symptoms of psoriasis. However their administration for a long period of time, which is necessary in such treatment causes tachyphylaxis so that either the dose has to be increased or stronger drugs have to be used leading to atrophy and achromasia or loss of pigmentation of peripheral normal skin, when it is topically applied on psoriatic lesion [*British National Formulary* (BNF), March 2001, No. 41].

Use of phototherapy (irradiation with ultraviolet radiation) or photochemotherapy, which consists of external or internal administration of psoralens and application of long wave ultraviolet rays to the affected part, is associated with disadvantages like the possibility of accelerated aging or pigmentation of the skin and of inducing carcinogenesis [*British National Formulary* (BNF), March 2001, No. 41].

External use of coal tar, even though is associated with fewer side effects when compared with steroids, is, however, messy and the drawbacks include strong odour, staining of skin etc. Occasionally it may cause stimulant dermatitis.

Methotrexate, even though it is a drug of choice for treating psoriatic conditions, needs to be closely monitored because it can cause liver damage and/or decrease the production of oxygen carrying red blood cells, infection-fighting white blood cells and clot-enhancing platelets. The long-term use of psoralens and methotrexate significantly increase the risk of squamous cell carcinoma in patients with psoriasis [Stern R. S., and Laird N., *Cancer*, 1994, 73, 2759].

The retinoids such as etretinate are taken internally by patients suffering from intractable psoriasis; however it is teratogenic and likely to accumulate in the body for a longer period of time and hence it is contraindicated in case of pregnancy [Stern R. S., and Laird N., *Cancer*, 1994, 73, 2759].

Use of macrocyclic immunosuppressive agents such as Cyclosporine, Tacrolimus and Ascomycin may impair kidney function or cause hypertension. Possible side effects of hydroxyurea include anemia and a decrease in white blood cells and platelets.

Calcipotriol, a synthetic vitamin D3 analogue has become one of the widely prescribed treatments for psoriasis. However, it causes significantly more skin irritation than potent topical corticosteroids. The common adverse effects include lesional or perilesional irritation, facial or scalp irritation, or excerbation of psoriasis [Ashcroft D. M., Wan Po A. L., Williams H. C. and Griffiths C. E. M., *BMJ*, 2000, 320, 963].

Current biotechnology approaches to psoriasis treatment relate to a direct pharmaceutical-mediated attack, either on cell proliferation or on the immune component of the disease. Immunosuppressive immunobiologicals such as Clenoliximab, MEDI-507, ICM3, IDEC-114, SMART Anti-CD3, Zenapax, Amavive, Hul 134, Xanelim, HuMaxCD4, IC747, IDEC-114 IDEC-131, Nuvion, DAB389IL-2, ONTAK and Etarnercept, known to block immune responses at various stages are currently under different phases of clinical trials.

None of the abovementioned treatments are, however, universally safe and effective. The magnitude of the impact of psoriasis is similar to that of other diseases like depression, hypertension and congestive heart failure. The cost of treating the disease averages 800 USD per patient per year in the United States, and the disease can cause significant loss in productivity [Feldman S. R., *American Academy of Dermatology*, August 2000].

Further, the disease owing to its sporadic course, gives variable response to treatments, which may also have adverse effects. Hence, it is a difficult disease to cure. The devastating nature of psoriasis is emphasized by the extent of the side effects that disease sufferers are willing to endure to attain a remission to a disease that they know will recur sooner or later.

In addition, apart from the clinical manifestations and inconvenience, the psychological impact of the disease on the patient's life is tremendous. Psoriasis is a complex condition affecting all aspects of emotion and physical debilitation for the patient and, substantially reduces the quality of life for millions of people all over the world. Moreover, as it is often clearly visible, affected individuals suffer marked distress, embarrassment and discomfort [Fortune D. G., Richards H. L., Main C. J., and Griffiths C. E. M., *J. Am. Acad. Dermatol.*, 1998, 39, 196].

A composition derived from a plant source, which provides a safe, well-tolerated and effective treatment of psoriasis and which moreover, overcomes the shortcomings and limitations of the current treatments has been disclosed in our US Patent Publication No. 2003/0194456 A1.

US Patent Publication No. 2003/0194456 A1 discloses useful in vitro and in vivo immunological and pharmacological activities of a medication/composition comprising an extract obtained from the leaves and/or stems of the plant, *Argemone mexicana*, optionally in combination with an extract obtained from the fruits of the plant, *Cuminum cyminum* for the treatment and prophylaxis of psoriasis and other disorders. The extract, which can be an aqueous, ethanolic or aqueous-ethanolic extract, apart from exhibiting useful immunological and pharmacological activities provides significant reduction in the rate of Psoriasis Area and Severity Index (PASI) score with better tolerability within the range of normal permissible limits. In proof of concept studies conducted on patients having chronic plaque type psoriasis, a composition comprising the abovementioned extract when administered orally was found to result in reduction of the PASI score from 6.33±2.84 to 0.90±1.27, with a disease free state observed in some patients after 8 weeks of treatment.

US Patent Publication No. 2003/0194456 A1 further reports the acute toxicity ($LD_{50}$) of the extract obtained from the leaves and/or stems of the plant, *Argemone mexicana*, as evaluated in mice and rats through oral and i.v. routes of administration to be >1000 mg/kg body weight of the animal with 50% mortality.

It might be mentioned herein that the *Argemone mexicana* plant is composed of various compounds, which include inter alia:

i) Alkaloids such as protopine, protopine nitrate, berberine, berberine nitrate, cryptopine, allocryptopine, coptisine, sanguinarine, dihydrosanguinarine, norsanguinarine, 6-acetonyl dihydrosanguinarine, dihydrochelerythrine, chelerythrine, norchelerythrine, 6-acetonyl dihydrochelerythrine, (−) cheilanthifolin, (−)-β-scoulerine methohydroxide, (−)-α-stylopine (−)-α and β-stylopine methohydroxides, (−)-cheilanthifolin, 6-acetonyl dihydrosanguinarine, (−)-α-tetrahydropalmatine methohydroxide, reticuline, thalifoline, muramine, argemonine, norargeminine, argemexicaine A, argemexicaine B, N-demethyloxysanguinarine; (+)-1,2,3,4-tetrahydro-1-(2-hydroxymethyl-3,4-dimethoxyphenylmethyl)-6,7-methylenedioxy-isoquinoline, helleritrine, and oxyhydrastinine;

ii) Flavonoids, such as isorhmanetin, isorhamnetin-3-glucoside; isorhamnetin-3-O-glucoside, isorhamnetin-3,7-diglucoside; 3-methoxy quercetin, quercetin 5,3',4' trimethyl ether; luteolin, argemexitin and eriodictyol;

iii) Fatty acids, such as palmitic, stearic, arachidic, oleic, linoleic, lauric, behenic, lignoceric, hexadecenoic, ricinoleic, 11-oxo-triacontanoic and 11-hydroxy triacontanoic;

iv) Amino acids, such as histidine, lysine, glutamic acid, glycine, alanine, leucine, valine, phenyl alanine, tyrosine, threonine, arginine, serine, asparagine, cysteine, methionine, tryptophan, hydroxyproline, proline, L-glutamine, hydroxyproline, β-alanine, and aspartic acid;

v) Carbohydrates, such as glucose and fructose and glycosides;

vi) Organic acids, such as succinic, citric, tartaric, maleic, and malic; and (vii) Other compounds like ceryl alcohol, β-sitosterol, potassium nitrate, calcium phosphate and calcium sulphate.

It has been found that the extract obtained from the leaves and/or stem of *Argemone mexicana* plant using the process for extraction eg. maceration and percolation, using water, ethanol and mixtures thereof disclosed in US Patent Application Publication No. 2003/0194456 A1 contains substantially all of the abovementioned compounds. In other words, the extract is composed of all the compounds present in the parts of the plant used for extraction i.e. it is composed of a mixture of alkaloids, flavonoids, fatty acids, organic acids, amino acids, sugars and salts.

The extracts, thus obtained as per the process described in US Patent Application Publication No. 2003/0194456 A1 were found to exhibit in vitro and in vivo immunological and pharmacological activities eg. immunosuppression, lymphoproliferation inhibition, cytokine modulation such as IL-2 inhibition, IFNγ inhibition, and IL-10 induction; keratinocyte proliferation inhibition, keratolytic activity, endothelial cell proliferation inhibition, inhibition of cell adhesion molecule expression such as ICAM-1, MEST inhibition, and enzymes inhibition such as p60src Tyrosine kinase, which are known to be involved in anti-psoriatic activity.

Furthermore, US Patent Application Publication No. 2003/0194456 A1 teaches that the abovementioned extracts of the leaves and/or stem of *Argemone mexicana* plant could be fractionated using alcoholic solvents such as n-butanol and methanol and the fractions obtained thereof also exhibit in vitro and in vivo immunological and pharmacological activities including anti-psoriatic activity.

The fractionation procedure of the aqueous extracts of the leaves and/or stem of *Argemone mexicana* plant, described in Patent Application Publication No. 2003/0194456 A1 was achieved through a multi-step, liquid-liquid partition chromatography, precipitation and drying of extracts and provides fractions containing substantially different classes of compounds as major components.

For instance, as per the method described in US Patent Application Publication No. 2003/0194456 A1 an n-butanol soluble fraction was prepared by adding n-butanol to the aqueous extract of the leaves and/or stem of *Argemone mexicana* plant, separation of the n-butanol layer from the aqueous phase, followed by washing of the n-butanol layer with water and evaporation of the solvent under reduced pressure to give the n-butanol-soluble fraction as a viscous mass. The aqueous layer, was mixed with methanol, wherein precipitation of a solid mass was effected. The solid mass was separated, and the mass dissolved in water and lyophilized to give the methanol-insoluble fraction. The filtrate obtained after separation of the methanol-insoluble precipitate from the methanol-water mixture on evaporation gave the methanol-soluble fraction as a solid mass.

Typically, *Argemone mexicana* plant yielded about 3-4.5% of n-butanol-soluble fraction; 46-54% of methanol-soluble fraction, having a total base number between 290-340; and 24-30% of methanol-insoluble fraction, having a total base number between 350-380. As used herein base number is the quantity of acid that is required to neutralize all basic constituents present in 1 g of sample.

As mentioned hereinbefore, the three fractions differ substantially in the constitution of compounds contained therein. The n-butanol-soluble fraction was found to contain alkaloids, flavonoids and other low molecular weight compounds; the methanol-soluble fraction was found to contain amino acids, organic acid and salts; while the methanol-insoluble fraction was found to contain sugars, organic acids and salts.

Even though, extensive chemical investigations over the years on different parts of the *Argemone mexicana* plant have resulted in the isolation of a number of alkaloids, flavonoids, amino acids, organic acids, fatty acids etc., however, no systematic study has been conducted and reported for isolation and identification of other principles present in the plant.

One such principle, commonly found in the plant kingdom is Arabinogalactan-Proteins (AGP), which are essentially macromolecules of polysaccharides in which the carbohydrate is associated with or linked to proteins. AGP is composed mainly of arabinose and galactose residues. These occur in plants as polysaccharides in association with varying amounts of proteins, and generally contain a high proportion of carbohydrates with comparatively less proportion of proteins, usually less than 10 of proteins, although, AGPs having higher contents of proteins are also known. AGPs are widely distributed in most of the higher plants such as *Echinacea purpurea, Nicotiana alata, Vitis vinifera, Diospyros kaki, Gladiolus gandavensis, Lolium multiflorum* [Anderson, R. L., Clarke, A. E., Jermyn, M. A., Knox, R. B. and Stone, B. A., Australian *J. Plant Physiol.*, 1977, 4, 143-158], *Phaseolus vulgaris* [Hawes, G. B., Adams, G. A., *Phytochemistry*, 1972, 11, 1461-1465] and *Acacia arabica* [Classen, B., Witthohn, K., and Blaschek, W., *Carbohydrate Research*, 2000, 327, 497-504].

AGPs possess adhesive and water holding properties and respond to wounds and infections in plants. These determine cellular identity and specific interactions. They also play a role in cell and tissue differentiation as well as in controlling somatic embryogenesis. They are also valued for various biological activities [WO 01/00682 A1, 2001]. There are two types of AGPs, viz. AGP I and AGP II. The latter i.e. AGP II contain a galactose core and are highly branched, contain usually less than 10% proteins and possess side chains highly substituted by arabinofuranosyl residues and sometimes other sugars like rhamnose, glucose, mannose etc. Presence of uronic acids and substituted derivatives are also reported.

As mentioned hereinbefore, even though, chemical investigations on all parts of *Argemone mexicana* have been conducted, however, no study has been directed towards isolation, characterization and understanding of the biological properties of AGPs present in certain parts of the plant.

SUMMARY OF THE INVENTION

The present invention provides a selective method for isolation of AGPs from an extract obtained from the leaves and/or stems of the plant, *Argemone mexicana* in purified form, which exhibits vastly superior anti-psoriatic activity and other useful immunological and pharmacological activities compared to the extract and fractions of the leaves and/or stems of the plant, *Argemone mexicana*, as disclosed in US Patent Application Publication No. 2003/0194456 A1. In particular, the vastly superior anti-psoriatic activity exhibited by the purified AGPs obtained by the selective method is found to be highly useful in preparation of a pharmaceutical composition comprising the same and thereby providing a safe, effective and well-tolerated treatment and form the basis of the present invention.

Therefore, an aspect of the present invention is to provide a selective method for isolation of purified Arabinogalactan-Protein (AGP) composition in a highly pure form from the leaves and/or stems of *Argemone mexicana* plant. In another aspect, the present invention provides a purified Arabinogalactan-Protein (AGP) composition, having an average molecular weight range between 10 KD to 150 KD, isolated from the leaves and/or stems of *Argemone mexicana* plant.

Another aspect of the present invention is to provide an anti-psoriatic composition and treatment for psoriasis, obtained from the leaves and/or stems of *Argemone mexicana* plant, which not only is highly safe, effective and well-tolerated but moreover, overcomes the shortcomings and limitations of the current therapeutic regimen.

Another aspect of the present invention is to provide a purified Arabinogalactan-Protein (AGP) composition isolated through a selective method from the leaves and/or stems of *Argemone mexicana* plant which exhibits useful immunological and pharmacological properties such as one or more of immunosuppression, lymphoproliferation inhibition, cytokine modulation such as IL-2 inhibition, IFN-γ inhibition, or IL-10 induction, keratinocyte proliferation inhibition, keratolytic activity and MEST inhibition.

Yet another further aspect of the present invention is to provide a purified Arabinogalactan-Protein (AGP) composition isolated through a selective method from the leaves and/or stems of *Argemone mexicana* plant for treatment or prophylaxis of one or more of disorders such as dermatitis; scleroderma; eczema; inflammatory disorders and other autoimmune diseases like psoriatic arthritis, rheumatoid arthritis, Crohn's disease, multiple sclerosis, irritable bowel disease, ankylosing spondilitis, systemic lupus erythrometosus and Sjogren's syndrome; and/or allergies like asthma and chronic obstructive pulmonary disease.

Yet another aspect of the present invention is to provide a pharmaceutical composition that can be used for the treatment and/or prophylaxis of the aforementioned diseases and conditions comprising the purified Arabinogalactan-Protein (AGP) composition isolated through a selective method from the leaves and/or stems of *Argemone mexicana* plant.

DETAILED DESCRIPTION OF THE INVENTION

Unless otherwise defined, all technical and scientific terms have the same meaning as commonly understand by one of ordinary skill in the art to which this invention below.

As used herein the phrase "purified Arabinogalactan-Protein (AGP) composition" means a composition consisting essentially of only arabinogalactan-proteins which may include trace amounts of other components obtained from extraction of the stem and/or leaves of *Argemone mexicana* plant according to this invention. The purified AGP composition is distinguished from a pharmaceutical composition comprising AGP composition because the purified AGP composition does not include any pharmaceutically acceptable excipients.

In our US Patent Application Publication No. 2003/0194456 A1 a process was disclosed for obtaining an extract from the leaves and/or stems of the *Argemone mexicana* plant and fractionation of the extract with n-butanol and methanol to give the respective n-butanol-soluble, methanol-soluble and methanol-insoluble fractions.

The method for preparation of the various fractions of the stem and/or leaves of the *Argemone mexicana* plant as disclosed in US Patent Application Publication No. 2003/0194456 A1 comprises the steps of:

i) Preparation of an extract of the stem and/or leaves of the *Argemone mexicana* plant, through a number of extraction procedures, however, preferably through a multi-step, successive maceration and percolation using solvents such as water, ethanol or mixtures thereof at room temperature to obtain the corresponding extracts, which are constituted of alkaloids, flavonoids, amino acids, organic acids, sugars and salts. These extracts could be used as such or were subjected to lyophilization to give a lyophilized mass, both of which were used for fractionation;

ii) Partitioning of the extract as obtained or a solution of the lyophilized mass in water as obtained in step i) with n-butanol, and separation of the n-butanol layer from the aqueous phase, followed by washing of n-butanol layer with water and evaporation of the solvent under reduced pressure to give a viscous mass of the n-butanol-soluble fraction, which is constituted primarily of alkaloids, flavonoids and other low molecular weight compounds;

iii) Mixing and agitation of the aqueous layer from step ii) with approximately six to seven times its volume of methanol and filtration/centrifugation of the precipitated solids and drying to give the methanol-insoluble fraction, which is constituted primarily of polysaccharides, organic acids and salts. This material was dissolved in water and lyophilized to give a lyophilized powder; and iv) Concentration of the filtrate i.e. aqueous methanolic solution from step iii) under reduced pressure to give a solid mass of the methanol-soluble fraction, which is constituted primarily of amino acids, organic acids and inorganic salts.

The methanol-insoluble fraction prepared according to the method disclosed in US Patent Application Publication No. 2003/0194456 A1 was isolated in a yield of about 33%. While there is mention in the specification that the fraction is constituted of sugars, organic acids and salts, however, these constituents were not characterized at that time.

Present investigations reveal that the methanol-insoluble fraction obtained as per the method disclosed in US Patent Application Publication No. 2003/0194456 A1 is constituted of approximately 3% by weight of AGPs, (with respect to the aqueous extract), the remaining constituents being organic acids, amino acids and inorganic salts i.e. the methanol-insoluble fraction obtained according to the method disclosed in US Patent Application Publication No. 2003/0194456 A1 is constituted of AGPs in mixture with other components. The methanol-insoluble fraction contains AGPs, albeit in low concentration and in a highly impure form.

The present inventors have found that AGPs can be isolated in a purified form in a yield of approximately 0.06% yield with respect to the stems and/or leaves of *Argemone mexicana* or approximately 1% with respect to the lyophilized aqueous extract prepared therefrom through a highly selective method and that the isolated AGPs exhibit vastly superior anti-psoriatic activity over the ones obtained through the method disclosed in US Patent Application Publication No. 2003/0194456 A1.

The selective method for isolation of the AGPs in purified form from the leaves and/or stems of the *Argemone mexicana* plant comprises the steps of:

a) extraction of 1 wt part of the leaves and/or stems of *Argemone mexicana* plant with 1 to 10 wt part of water, a $C_1$-$C_3$ alcohol or a mixture thereof to obtain an aqueous extract which can be but does not have to be partially or completely concentrated or lyopholized;

b) removal of the basic and acidic components from the aqueous extract, partially concentrated extract, an aqueous solution of the completely concentrated extract or lypholized extract obtained in step a) by subjecting the partially concentrated extract or the aqueous solution of the concentrated extract to ion exchange chromatography to obtain a neutral aqueous extract;

c) fractionation of the neutral aqueous extract obtained in step b) with n-butanol to give a n-butanol-soluble fraction;

d) mixing and agitation of the aqueous washes from step c) with methanol or ethanol and isolation of the precipitated solids to obtain the methanol or ethanol-insoluble fraction; and e) subjecting the methanol or ethanol-insoluble fraction obtained in step d) to gel chromatography and size exclusion chromatography in succession to obtain purified Arabinogalactan-Protein (AGP).

The selective method for isolation of the purified AGP is summarized in FIG. 1.

For extraction, leaves, stems or both of the *Argemone mexicana* plant can be used. Preferably fresh leaves, stems or both are used, and these are ground to a coarse or fine paste prior to extraction.

In an embodiment of the invention, one wt part of the fresh ground leaves and/or stems of *Argemone mexicana* are extracted with 1 to 10 wt parts of water, $C_{1-3}$ alcohol, or a mixture thereof 2 to 4 times and the combined extracts percolated for 2 to 20 hours at a temperature of between 20° C. to 45° C. In another embodiment, one wt part of the fresh ground leaves and/or stems of *Argemone mexicana* are extracted with 1 to 3 wt parts of water, $C_{1-3}$ alcohol, or a mixture thereof 2 to 4 times and the combined extracts percolated for 2 to 16 hours at a temperature of between 20° C. to 45° C.

In another embodiment, one wt part of the fresh ground leaves and/or stems of *Argemone mexicana* are extracted with 1 to 1.5 wt part of water, a $C_{1-3}$ alcohol, or a mixture of water and the $C_{1-3}$ alcohol thereof, 2 to 4 times and the combined extracts percolated for 16 hours at room temperature.

The $C_1$-$C_3$ alcohol is selected from methanol, ethanol, 1-propanol and 2-propanol, preferably ethanol.

After percolation, the extract is filtered or centrifuged and the filtrate can be partially concentrated to a certain volume of the original volume of the extract or can be concentrated to dryness or can be lyophilized.

When the extract is partially concentrated it is concentrated to a volume of between $\frac{1}{5}^{th}$ to $\frac{1}{10}^{th}$ of the original volume of the extract. When the original extract is concentrated to dryness or lyophilized, the dried extract or the lyophilized powder can be redissolved in 12 to 50 times by wt of water to one part by wt of the dried/lyophilized mass prior to ion exchange chromatography.

In a preferred embodiment the lyophilized aqueous extract was dissolved in 12 times water prior to ion exchange chromatography.

Either the solution of the partially concentrated extract or the aqueous solution of the concentrated or lyophilized obtained on complete concentration of the original extract is then subjected to sequential ion exchange chromatography over a cation exchange resin followed by chromatography over an anion exchange resin or in another embodiment ion exchange chromatography over an anion exchange resin followed by chromatography over a cation exchange resin to afford a neutral aqueous extract.

The cation and anion exchange resins are employed in proportions of 1 part to 50 parts by wt to the volume of the extract used.

Suitable cation exchange resins that can be employed include sulphonated polystyrene strong-acid cation exchangers and carboxylic acid-type weak acid cation exchangers. Suitable cation exchange resins include but are not limited to commercially available and commonly used sulphonated polystyrene strong-acid cation exchangers like AG 50W (Bio-Rad, USA), Amberlite IR-20 (Rohm and Haas, USA), Dowex 50W (Dow Chemical Co., USA), Duolite 225 (Dia-Prosim Ltd), Permutit RS (Permutit AG, Germany), and Permutite C50D (Philips and Pain-Vermorel, France); and carboxylic acid-type weak acid cation exchangers like Amberlite IRC-50 (Rohm and Haas, USA), Bio-Rex 70 (Bio-Rad, USA), Chelax 100 (Bio-Rad, USA), Duolite 436 (Dia-Prosim Ltd), Permutit C (Permutit AG, Germany), and Permutit H and H-70 (Permutit Co., USA).

Suitable anion exchange resins that can be employed include aliphatic amine-type weak base anion exchangers and strong base anion exchangers. The anion exchange resins include but are not limited to the commercially available and commonly used aliphatic amine-type weak base anion exchangers like Amberlites IR-45 and IRA-67 (Rohm and Haas, USA), Dowex 3 (Dow Chemical Co., USA), Permutit E (Permutit AG, Germany), Permutit A 240A (Philips and Pain-Vermorel, France); and strong base anion exchangers like AG 2x8 (Bio-Rad, USA), Amberlite IRA-400 (Rohm and Haas, USA), Dowex 2×8 (Dow Chemical Co., USA), Duolite 113 (Dia-Prosim Ltd), Permutit ESB (Permutit AG, Germany), and Permutite 330D (Philips and pain-Vermorel, France).

The neutral aqueous extract thus obtained can be lyophilized and the lyophilized mass can be partitioned between n-butanol and water for the next fractionation step. In the alternative, the neutral aqueous extract can be used as such for fractionation with n-butanol. For cost-effectiveness, it is preferable to use the solution of neutral fraction obtained after passing through cation and anion exchange resins as such for fractionation with n-butanol.

Typically, the abovementioned lyophilized mass of the neutral extract is partitioned in a mixture of water and n-butanol per 1 part of the lyophilized mass. The solution is allowed to stand and the n-butanol layer separated from the aqueous phase. The step is repeated 2 to 4 times and the combined aqueous layers are used for further fractionation with methanol or ethanol.

In an example of the invention 1 part by volume of the solution of neutral aqueous fraction obtained after passing through cation (Amberlite IR 120) and anion (Amberlite IRA 400) exchange resins is added to about 10 parts by volume of n-butanol. The phases are mixed, allowed to stand and the n-butanol layer separated from the aqueous phase. The step is repeated 2 to 4 times and the combined aqueous layers are used for further fractionation with methanol or ethanol.

The combined aqueous phase obtained in the abovementioned step is mixed with methanol or ethanol and agitated to precipitate out the methanol/ethanol-insoluble fraction. Typically, methanol or ethanol is employed in proportions of 1 to 20 times volume per 1 volume of the aqueous extract.

The precipitated solid, which contains the AGP is isolated by conventional means, such as decantation, filtration, centrifugation, etc. and then dried to yield a brownish amorphous powder.

The solid AGP thus obtained, which contains AGP-HM and AGP-LM is further subjected to sequential gel chromatography and size exclusion chromatography to obtain purified AGP-HM and AGP-LM.

The gel chromatography is carried out using conventional techniques and polymeric adsorbents such as AMBERLITE® polymeric adsorbents like XAD-2®(polystyrene), XAD-4®(polystyrene) or XAD-7®(acrylic ester), preferably XAD-7®. The impure solid AGP is applied in a narrow band at the top of the requisite column and washed by the mobile phase, which is water. The fractions containing the AGP are collected.

The elute containing the impure AGP is further subjected to size exclusion chromatography using conventional techniques. Sephacryl (1:25-1:50) may be used to obtain purified AGP, AGP (HM) and AGP (LM) of the present invention. Commercially available Sephracyl S-100, S-200 HR and S-300 HR can be used, the preferred one being S-200 HR. The Sephracyl can be employed in a ratio of 1 to 2 parts by weight to 25 to 250 parts by volume of the solution of AGP obtained after gel chromatography.

In an embodiment, the crude AGP (100 mg) is dissolved in water and loaded on sephacryl S-200 (25 ml). The column is eluted at a rate of 0.5 ml/minute and fifty fractions were collected. All fractions were monitored by HPLC-ELSD. Fractions 10 to 20 were combined on the basis of HPLC to yield AGP-HM and fractions 25 to 35 were also combined to yield AGP-LM, the components of AGP composition having an average molecular weight range between 10 KD to 150 KD.

Following size exclusion chromatography, the purified AGP of the present invention can be isolated from the aqueous solution through employment of conventional techniques such as evaporation, lyophilization, spray drying, freeze drying etc.

The purified AGP, thus obtained is found to show an average molecular weight range between 10 KD to 150 KD. It is found to exhibit one or more of the following effects: immunosuppression, lymphoproliferation inhibition, cytokine modulation such as IL-2 inhibition, IFN-γ inhibition, IL-10 induction, keratinocyte proliferation inhibition, keratolytic activity and MEST inhibition. These are known to be involved in inflammatory disorders, autoimmune diseases and allergies. These are also known to be involved in antipsoriatic activity, dermatitis, scleroderma, eczema and scaly itchy patches. Inflammatory disorders and autoimmune diseases include psoriatic arthritis, rheumatoid arthritis, Crohn's disease, multiple sclerosis, irritable bowel disease, ankylosing spondilitis, systemic lupus erythrometosus, Sjogren's syndrome. Types of psoriasis include plaque psoriasis, guttate psoriasis, pustular psoriasis and psoriasis of the nails. Allergies include asthma and chronic obstructive pulmonary disease. IL-10 induction is also useful in other chronic, recurrent and other skin ailments where cutaneous lymphocyte antigen or cutaneous leukocyte antigen is involved.

The purified Arabinogalactan-Protein (AGP) composition exhibits excellent antipsoriatic activity in vitro and in vivo, mediated via IL-10 induction.

The purified AGP of the present invention (which is water-soluble) obtained after size exclusion chromatography over, for example, sephacryl is constituted of several fractions of differing molecular weights. Such fractions have average molecular weights as high as between 115 to 150 KD and as low as between 10 to 15 KD. The AGPs possessing high molecular weights are termed as AGP-HM, while those of low molecular weights are termed as AGP-LM. A typical AGP composition is thus constituted of AGP-HMs and AGP-LMs in varying proportions. It should be understood that the aforementioned AGP is formed through a biogenetic pathway, wherein the carbohydrates/monosaccharides are constantly seeking a protein for covalent bond formation, leading ultimately to low molecular weight (AGP-LMs) and high molecular weight (AGP-HMs) AGPs. Such a covalent bond formation is constantly propagated and whether in one particular method one ends up with an AGP-LM of average molecular weight less than 10 KD or an AGP-HM of average molecular weight greater than 150 KD would depend on several factors, which are to name a few the nature of the parts of the plant used i.e. whether fresh leaves or stems of the *Argemone mexicana* plant has been used for extraction, the harvesting conditions of the leaves i.e. whether harvested in the rainy season etc. Hence, it is possible that a purified AGP composition having an average molecular weight outside the range of 10 KD to 150 KD could be obtained employing the method of the present invention depending on the abovementioned factors. In view of the above, AGP composition with an average molecular weight outside the range of 10 KD to 150 KD would still be within the scope of the invention. Examples of such AGP compositions are those with a lower limit of an average molecular weight of 9 KD or AGP compositions with an upper limit of average molecular weight to 155 KD.

The bulk of the AGP obtained by the present method is constituted of carbohydrates, with a smaller proportion of proteins. The carbohydrate components of the AGP are Arabinose, Rhamnose, Methylated Uronic acid, Mannose, Galactose, Glucose and other unidentified sugars, which are linked to a protein component consisting of various amino acids, which are identified as Asparagine, Glutamine, Hydroxyproline, Serine, Glycine, Histidine, Arginine, Threonine, Alanine, Proline, Tyrosine, Valine, Methionine, Isoleucine, Leucine, Lysine, Phenylalanine etc., as would be evident from Tables-I and II of the specification.

It is noticed that not only is the glycosyl composition of both the AGP-HMs and AGP-LMs similar i.e. they show similarity in the ratio of monosaccharides and proteins present therein but the glycosyl linkage in both the cases are also similar.

Further, it is noted that the biological activity of both the two molecular weight components are comparable and do not show much variation. That is to say, a purified AGP-LM having a molecular weight of 10 KD exhibits one or more of immunosuppression; lymphoproliferation inhibition; cytokine modulation such as IL-2 inhibition, IFN-γ inhibition, and IL-10 induction; keratinocyte proliferation inhibition, keratolytic activity, MEST inhibition and most importantly anti-psoriasis activity which is comparable to those exhibited by a purified AGP-HM having a molecular weight of 150 KD.

The AGP composition of this invention is composed of AGPs (both AGP-HM and AGP-LM) which is substantially free of other components present in the extract of the plant, which are a mixture of alkaloids, flavonoids, organic acids, amino acids, sugars, polysaccharides, proteins, proteoglycans (excluding AGP) and salts. As used herein the term "substantially free" is intended to cover AGP compositions containing from about 0.0001% by weight to about 10% by weight of other components of the extract of the plant.

The n-Butanol fraction contains a mixture of alkaloids (such as protopine, protopine nitrate, berberine, berberine nitrate, cryptopine, allocryptopine, coptisine, sanguinarine, dihydrosanguinarine, norsanguinarine, 6-acetonyl dihydrosanguinarine, dihydrochelerythrine, chelerythrine, norchelerythrine, 6-acetonyl dihydrochelerythrine, (−) cheilanthifolin, (−)-β-scoulerine methohydroxide, (−)-α-stylopine methohydroxide, 6-acetonyl dihydrosanguinarine, (−)-α-tetrahydropalmatine methohydroxide, reticuline, thalifoline, muramine, argemonine, norargeminine, helleritrine, and oxyhydrastinine), flavonoids (such as isorhmanetin, isorhamnetin-3-glucoside and isorhamnetin-3,7-diglucoside) and other low molecular weight compounds;

The Methanol-soluble fraction contains amino acids (such as histidine, lysine, glutamic acid, glycine, alanine, leucine, valine, phenylalanine, tyrosine, threonine, arginine, serine, asparagine, cysteine, methionine, tryptophan, hydroxyproline, proline and aspartic acid), sugars and some salts; and The Methanol-insoluble fraction contains some organic acids (such as succinic, citric, tartaric and malic), monosaccharides, polysaccharides, proteoglycans (including AGP) and salts.

In an embodiment of the invention, the AGP compositions contain less than 1% by weight of other components of the extract of the plant.

The purified AGP composition isolated by the process of this invention is found to be an excellent inducer for IL-10 in ConA activated human PBMCs. It produced about 371% induction at a concentration of 200 μg/ml, which is vastly superior to a value of about 171% exhibited by the methanol-insoluble fraction obtained through the method disclosed in US Patent Application Publication No. 2003/0194456 A1 at the same concentration of 200 μg/ml.

More particularly, the isolated AGP composition is remarkable in that it exhibits IL-10 induction equal to or greater than that exhibited by the methanol-insoluble fraction obtained through the method disclosed in US Patent Application Publication No. 2003/0194456 A1 even at a very low concentration of 0.2 to 2.0 μg/ml.

A comparison of the effect of concentration of the AGP of the present invention on IL-10 Induction by ConA Induced Human PBMCs with that of the Methanol-Insoluble Fraction Prepared by the Method Described in US Patent Application No. 2003/0194456 A1 is summarized in Table-IA

TABLE IA

Comparison of the Effect of the AGP Composition of the Present Invention on IL-10 Induction by ConA Induced Human PBMCs with that of the Methanol-Insoluble Fraction Prepared by the Method Described in U.S. patent application No. 2003/0,194,456 A1.

| Sr. No. | Concentration of the AGP Composition of the Present Invention (μg/ml) | Average Percent Induction | Concentration of the Methanol-Insoluble Fraction obtained by the Method of U.S. application No. 2003/0,194,456 A1 | Average Percent Induction (As given in Table-8 of U.S. application No. 2003/0,194,456 A1 |
|---|---|---|---|---|
| 01 | 200.00 | 371.40 | 200.00 | 171.10 |
| 02 | 20.00 | 303.80 | 20.00 | 162.10 |
| 03 | 2.00 | 237.30 | 2.00 | 98.30 |
| 04 | 0.20 | 137.20 | 0.20 | 24.60 |
| 05 | 0.02 | 114.30 | 0.02 | −4.00 |
| 06 | 0.002 | 106.00 | 0.002 | −5.00 |
| 07 | 0.0002 | 102.60 | 0.0002 | — |

*The values are depicted in percent increase from basal with reference to control.
**The Average % Induction exhibited by the methanol-insoluble fraction obtained through the method disclosed in U.S. patent application No. 2003/0,194,456 A1 was 171% at a concentration of 200 μg/ml.

Such vastly potent activity exhibited by the AGP obtained by the method described hereinbefore enables it to be administered at a substantially reduced concentration of $\frac{1}{100}^{th}$ to $\frac{1}{1000}^{th}$ of the dosage required to be administered using the extracts/fractions obtained by the method disclosed in US Patent Application No. 2003/0194456 A1 thereby providing a cost-effective, efficient and well-tolerated treatment for psoriasis and other disorders.

The present invention provides pharmaceutical compositions that comprise an effective amount of the purified Arabinogalactan-Protein (AGP) composition, having an average molecular weight range between 10 KD to 150 KD, isolated from the leaves and/or stems of *Argemone mexicana* plant by the selective method enumerated hereinabove, in admixture with pharmaceutically acceptable excipients. The compositions of this invention are safe, effective and well-tolerated.

Pharmaceutical compositions suitable for use in the present invention include compositions wherein the active ingredients are contained in an amount effective to achieve its desired purpose. The term an effective amount means that amount of AGP composition that will elicit the biological or medical response of a tissue, cell, system, animal, non-human mammal, or human mammal that is being sought. This is intended to refer to situations where there may be a slowing, interrupting, arresting or stopping of the progression of the diseases and/or conditions described herein, but does not necessarily indicate a total elimination of all disease and condition symptoms, but does include prophylactic treatment of diseases and/or conditions.

The AGP composition of the present invention can be formulated into a suitable dosage form in admixture with one or more pharmaceutically acceptable excipients such as carriers, diluents, fillers and the like. Suitable dosage forms are forms suitable for oral administration or topical application. Non-limiting examples of such dosage forms are liquids, dry powder or powdered concentrate, capsule, tablet, pellet, granules, gels, ointments, creams, emulsions, suspensions, dispersions, lotions, pills and the like.

Generally a typical pharmaceutical composition for oral administration comprises the AGP composition as active ingredient in an amount in the range between 50-5000 mg, more preferably 200 mg.

Generally a typical pharmaceutical composition for topical administration comprises the AGP composition as active ingredient in an amount in the range between 0.1-10% by weight, more preferably 2% by weight.

The prophylatic or therapeutic dose of the AGP composition or compositions containing AGP composition is from 50 mg and 5000 mg per day, preferably 200 mg dose per day. The dose may be administered as a single or divided dose.

However, the exact formulation, route of administration and dosage can be chosen by the patient or health care professional in view of the patient's condition and whether the patient is presently afflicted with the disease or condition or whether the treatment is prophylatic. A prophylatic dosage can be administered to a patient who is at risk for developing a disease or condition. The risk factors include but are not limited to genetic and environmental risk factors. It is preferred to administer the pharmaceutical composition at a dose that will produce the desired result without causing undue side effects. As used herein, the term "patient" means animal, non-human mammal, or human mammal.

Suitable dosage forms for oral administration and topical application comprising the AGP composition of the present invention in admixture with pharmaceutically acceptable carriers can be prepared.

Suitable forms of oral administration include tablets, capsules, powdered concentrate, syrups, elixirs or suspensions. Suitable forms of topical application include ointments, creams, lotions, oils or transdermal drug delivery systems.

Suitable pharmaceutically acceptable excipients include sugars such as lactose, sucrose, mannitol, sorbitol and xylitol; Starches such as corn starch, tapioca starch and potato starch; cellulose and its derivatives such as sodium carboxymethyl cellulose, ethyl cellulose and methyl cellulose; Calcium phosphates such as dicalcium phosphate and tricalcium phosphate; Sodium sulphate; Calcium sulphate; Polyvinylpyrrolidone; Polyvinyl alcohol; Stearic acid; Vegetable oils such as peanut oil, cottonseed oil, sesame oil, olive oil and corn oil; Non-ionic, cationic and anionic surfactants; Ethylene glycol polymers; β-cyclodextrin; Fatty alcohols; Hydrolysed cereal solids; as well as other Non-toxic compatible fillers, Binders, Disintegrants, Buffers, Preservatives, Antioxidants, Lubricants, Flavouring agents etc.

The compositions of this invention are prepared according to conventional techniques known in the art.

The compositions are pharmaceutically acceptable meaning that they are suitable for use with humans and/or animals.

The AGP compositions and pharmaceutical compositions of this invention are useful in the treatment and/or prophylaxis of the diseases and conditions described herein.

The AGP composition of this invention or a pharmaceutical composition comprising AGP composition of this invention can be used in the treatment and/or prophylaxis of psoriasis skin ailments such as psoriasis including plaque psoriasis, guttate psoriasis, pustular psoriasis and psoriasis of the nails comprising administration to a mammal in need of such treatment or a mammal at risk for psoriasis skin ailments an effective amount of the AGP composition or a pharmaceutical composition comprising a therapeutically effective amount of the purified Arabinogalactan-Protein (AGP) composition.

The AGP composition or a pharmaceutical composition comprising the AGP composition can be used in the treatment or prophylaxis of inflammatory disorders; autoimmune diseases like psoriatic arthritis, rheumatoid arthritis, Crohn's disease, multiple sclerosis, irritable bowel disease, ankylosing spondilitis, systemic lupus erythrometosus and Sjogren's syndrome; allergies like asthma and chronic obstructive pulmonary disease. The treatment or prophylaxis comprises administration to a mammal in need of such treatment or a mammal at risk for developing or experiencing an outbreak of one of these disorders or diseases an effective amount of the AGP composition or a pharmaceutical composition comprising a therapeutically effective amount of the purified Arabinogalactan-Protein (AGP) composition. Compositions of this invention which cause immunosuppression, are also useful for patients who expect to undergo or have received an organ transplant.

Structural Elucidation and Characterization of the AGP Composition

Determination of Carbohydrate Content of the AGP Composition

Total carbohydrate content of the AGP compositions, of the present invention was determined by phenol-sulphuric acid method using D-galactose as a standard. The AGP composition, AGP-HM and AGP-LM were dissolved separately in a concentration of 0.16 mg/ml with distilled water. To 1 ml each of the three solutions taken separately was added 1 ml of 5% phenol solution and 10 ml of sulphuric acid. These were vortexed to mix, allowed to cool till room temperature. Absorbance was measured at 480 nm. The carbohydrate content of the AGP compositions was found to be between 45-98% respectively as compared with the galactose standard.

Determination of Protein Content of the AGP Composition

Total protein content of the AGP compositions, of the present invention was determined by Bradford method. Protein content of the AGP composition, AGP-HM and AGP-LM was between 2-20%. The amino acid constituents of the AGP composition were identified as asparagine, glutamine, hydroxyproline, serine, glycine, histidine, arginine, threonine, alanine, proline, tyrosine, valine, methionine, isoleucine, leucine, lysine and phenylalanine, by amino acid analyzer using standards.

Identification of Glycosyl and Amino Acid Content of the AGP Composition by Hydrolysis and TLC 20 mg of neutral fraction obtained after size exclusion chromatography was taken and hydrolyzed with 2M trifluoro acetic acid (TFA, 200 μl) in a closed vial. The vial was heated at 100° C. for 1 hr, concentrated and lyophilized. A Thin Layer Chromatography (TLC) of the mixture was run with standard sugar and amino acid samples. The results observed showed the presence of monosaccharides such as arabinose, galactose, glucose, rhamnose and mannose. Amino acids such as valine, phenylalanine, serine, GABA, isoleucine and histidine were also observed.

Identification of Glycosyl Content of the AGP Composition

Glycosyl composition analysis was performed by combined gas chromatography/mass spectrometry (GC/MS) of the per-O-trimethylsilyl (TMS) derivatives of the monosaccharide methyl glycosides produced from the AGP-HM a and AGP-LM by acidic methanolysis.

Methyl glycosides were first prepared from dry sample of AGPs by methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (0.5 hours). These procedures were carried out as previously described by York, W. S., Darvill, A. G., McNeil, M., Stevenson, T. T., and Albersheim, P., *Methods Enzymol.*, 1985, 230, 1-15 and *Methods Enzymol.*, 1985, 118, 3-40.

GC/MS analysis of the TMS methyl glycosides was performed on an HP 5890 GC interfaced to a 5970 MSD, using an All Tech EC-1 fused silica capillary column (30 m×0.25 mm ID).

Table I summarizes the glycosyl components of AGP composition.

TABLE I

Glycosyl components of AGP composition

| Components | AGP Composition (Mole %) |
|---|---|
| Arabinose (Ara) | 34.00 |
| Rhamnose (Rha) | 3.40 |
| Methylated uronic acid (MUA) | 5.00 |
| Mannose (Man) | 2.20 |
| Galactose (Gal) | 48.90 |
| Glucose (Glc) | Not Detected |
| Unidentified sugars | 6.50 |

Determination of Glycosyl Linkage of AGP Composition

NaOH method: For glycosyl linkage analysis, a sample of AGP composition was permethylated, depolymerized, reduced, and acetylated; and the resultant partially methylated alditol acetates (PMAAs) analyzed by gas chromatography-mass spectrometry (GC-MS) as described earlier [York, W. S., Darvill, A. G., McNeil, M., Stevenson, T. T., and Albersheim, P., *Methods Enzymol.*, 1985, 230, 1-15; York, W. S., Darvill, A. G., McNeil, M., Stevenson, T. T., and Albersheim, P., *Methods Enzymol.*, 1985, 118, 3-40].

Initially, an aliquot of the sample was permethylated [by the method of Ciukanu and Kerek, *Carbohydr. Res.*, 1984, 131, 209-217] including treatment with sodium hydroxide and methyl iodide in dry DMSO. The permethylation was repeated twice in order to aid complete methylation of the polymer. Following sample workup, the permethylated material was hydrolyzed using 2 M trifluoroacetic acid (2 h in sealed tube at 121° C.), reduced with $NaBD_4$, and acetylated using acetic anhydride/pyridine. The resulting PMAAs were analyzed on a Hewlett Packard 5890 GC interfaced to a 5970 MSD (mass selective detector, electron impact ionization mode); separation was performed on a 30 m Supelco 2330 bonded phase fused silica capillary column.

Table-II summarizes the glycosyl linkages with percentages.

TABLE II

Glycosl Linkage of AGP Composition

| Glycosyl Residue | Percentage Present in the AGP Composition |
|---|---|
| terminal rhamnopyranosyl residue (t-Rha p) | 3.00 |
| terminal arabinofuranosyl residue (t-Ara f) | 22.00 |
| terminal arabinopyranosyl residue (t-Ara p) | 1.00 |
| Mixture | 1.00 |
| 3-rhamnopyranosyl residue (3-Rha p) | |
| 4-rhamnopyranosyl residue (4-Rha p) | |
| terminal glucopyranosyl residue (t-Glc p) | 3.00 |
| terminal galactopyranosyl residue (t-Gal p) | 5.00 |
| 5-linked arabinofuranosyl residue (5-Ara f) | 5.00 |
| 2-linked mannopyranosyl residue (2-Man p) | Trace |
| 2-linked glucopyranosyl residue (2-Glc p) | Trace |
| 3-linked galactopyranosyl residue (3-Gal p) | 16.00 |
| 4-linked galactopyranosyl residue (4-Gal p) | 1.00 |
| 6-linked glucopyranosyl residue (6-Glc p) | 2.00 |
| 6-linked galactopyranosyl residue (6-Gal p) | 8.00 |
| 3,6-linked glucopyranosyl residue (3,6-Glc p) | 2.00 |
| 3,6-linked galactopyranosyl residue (3,6-Gal p) | 31.00 |

Determination of Molecular Weight of the AGP Composition

AGP composition, AGP-HM and AGP-LM were analyzed using Waters aqueous GPC instrument, Model Alliance 2690 which is equipped with integrated solvent and sample management unit and refractive index detector containing thermally shielded flow cell & optics with counter current heat exchanger for better baseline stability. The chromatography workstation includes data acquisition and control software and Millenium software for data processing. The GPC columns are from Tosoh Corporation (TSK-GEL PW® Type) consisting of hydrophilic polymer based semi rigid gel. The exclusion limit for polysaccharides (Dextran) is from 1,000 to 7,000,00 molecular weight. These columns were designed for analytical and preparative separation of synthesized water soluble polymers, oligomers and biological substances such as polysaccharides, nucleic acids, proteins, peptides, etc. The pullulan kit consists of polysaccharide samples of different molecular weight for column calibration.

A GPC method has been developed using varying analytical conditions such as different porosity columns, concentration & nature of mobile phase, flow rate, detector sensitivity etc. The optimum separation with polysaccharide sample is obtained by using 0.2 M sodium nitrate solution and the following were suitable analytical conditions for the characterization of polysaccharide based drug molecule.

The molecular weight of AGP composition was determined by comparison of the elution time using size exclusion chromatography. Based on the comparison the average molecular weight range of AGP composition was found to be between 10 KD to 150 KD.

The molecular weights of AGP-LM and AGP-HM were also determined in a similar way. Based on the comparison the average molecular weight of the components were found to be 13 KD and 115 KD, respectively.

Fourier Transform Infrared (FT-IR) Spectrum of the AGP Composition

IR spectrum of the AGP-HM of the present invention measured by Fourier Transform Infrared Spectrometer (8201 PC Shimadzu) using Nujol mull in KBr pellets shows broad absorption band at 3400 cm$^{-1}$ indicating the presence of hydroxyl groups and at 2850-2960 cm$^{-1}$ revealing the stretching of CH bonds.

h) $^1$H Nuclear Magnetic Spectrum of the AGP Composition $^1$H NMR spectrum of the AGP of the present invention was recorded in D$_2$O at 500 MHz in Bruker DRX 500 Nuclear Magnetic Resonance Spectrometer.

An extensive proton assignment of all the major linkage types detected by methylation analysis was made. In the $^1$H NMR spectrum H-1 signals corresponding to the β-D-Gal-p residues (δ 4.22-4.47) and α-L-Ara-f residues (δ 5.17-5.33) were detected. There were numerous signals from δ 3.53-4.22, which corresponded to H-2 to H-6 of β-D-Gal p residues, H-2 to H-5 of the α-L-Ara f residues and H-2 to H-5 of small residues of glucose, rhamnose and mannose. To resolve and assign these signals to particular residues 2D homo- and heteronuclear experiments were performed. Assignment of the different linkage types to each of the spin systems identified in the 2D spectra was supported both by the linkage data in Table II and by comparison with the NMR data reported in literature for other AGPs.

Anomeric protons: The anomeric protons observed at δ 5.33 and δ 5.17 were assigned to terminal and 5-linked α-L-Ara f residues, respectively. Signal at δ 5.17 was also assigned to terminal α-L-Rha p and δ 5.10 to 4-linked α-L-Rha p. Similarly, the signal at δ 4.61 was assigned to 3-linked α-L-Rha p. The signal at δ 4.56 was assigned to 6-linked β-D-Gal p. Signal at δ 4.61 was assigned to 3-linked β-D-Gal p and the signals at δ 4.56 and 4.57 were assigned to terminal β-D-Gal p and 3-, 6-linked β-D-Gal p.

H-2 protons: Signals at δ 4.31 and 4.22 were assigned to H-2 of terminal and 5-linked α-L-Ara f residue, respectively. Further, signal at δ 3.45 was assigned to terminal β-D-Gal p while the signal at δ 3.74 was assigned to 3-, 6- and 3,6-linked β-D-Gal p residues. Signals at δ 4.03, 3.74 and 3.57 were assigned to H-2 protons of 4-linked, 3-linked and terminal α-L-Rha p, respectively.

H-3 protons: Signal at δ 4.03 was assigned to terminal and 5-linked α-L-Ara f residues. Further the signal at δ 3.81 was assigned to terminal and 6-linked β-D-Gal p. Similarly signal at δ 4.31 was assigned to 3- and 3,6-linked β-D-Gal p moieties. Signals at δ 3.93, 3.63 and 3.57 were assigned to 4-linked, terminal and 3-linked α-L-Rha p respectively.

H-4 protons: Signal at δ 4.22 was assigned to terminal and 5-linked α-L-Ara f. Signal at δ 3.63 was assigned to 3- and 6-linked β-D-Gal p residues. Further, signals at δ 3.86 and 4.03 were assigned to terminal and 3,6-linked β-D-Gal p, respectively. Similarly, signals at δ 3.63, 3.09 and 2.82 were assigned to 4-linked, 3-linked and terminal α-L-Rha p moiety.

H-5 protons: Signal at δ 3.81 was assigned to 6- and 3,6-linked β-D-Gal p. Similarly signal at δ 4.03 was assigned to terminal and 3-linked β-D-Gal p. Signals at δ 3.91 and 3.93 were assigned to terminal and 5-linked α-L-Ara f respectively. Signals at δ 4.22, 4.03 and 3.09 were assigned to H-5 of terminal, 4-linked and 3-linked α-L-Rha p. Signals at δ 4.03, 3.45 and 4.03 could be assigned to H-5 of 3-linked β-D-Gal p and terminal β-D-Gal p residues, respectively.

H-6 protons: Signal at δ 3.93 was assigned to 6- and 3,6-linked β-D-Gal p. Signals at δ 3.91 and 3.81 were assigned to terminal and 3-linked β-D-Gal p, respectively. The methyl protons observed at δ 1.03, 1.34 and 1.40 were assignable to 3-linked, 4-linked and terminal α-L-Rha p moiety.

The above assignments were further confirmed by carrying out HOMOCOSY experiments.

Amino acid residues: The methyl group for the amino acids valine, leucine and isoleucine were observed at δ 1.03 while the methyls assignable to threonine and alanine were located at δ 1.34 and 1.40, respectively.

Cα, Cβ (C—H, CH$_2$), Cγ (CH$_2$) and Cδ (CH$_2$) protons of arginine, asparagine, glutamine, isoleucine, leucine, lysine, methionine, proline and valine were observed between δ 1.3-2.8.

C-β (CH$_2$, CH), Cγ, Cδ protons of asparagine, histidine, phenylalanine and tyrosine were observed between δ 2.8-3.5.

Cα protons of alanine, arginine, glutamine, glycine, isoleucine, leucine, lysine, methionine, threonine and valine were observed between δ 3.5-3.9.

Cα protons of asparagine, histidine, phenylalanine, proline, serine, tyrosine and Cβ protons of serine and threonine were observed between δ 3.90-4.2.

Weak signals in the downfield region from δ 6.6-7.5 were assigned to N—H and aromatic protons of phenylalanine and tyrosine.

i) $^{13}$C Nuclear Magnetic Spectrum of the AGP Composition

Anomeric Carbons: In the $^{13}$C NMR spectrum the signals at δ 109.10 and 107.37 were assigned to the anomeric carbons of terminal and 5-linked α-L-Ara f moiety. Signals between δ 103-102 were assigned to anomeric carbons of terminal, 3-linked, 6-linked and 3,6-linked of β-D-Gal p residues. The same overlapping signals between δ 103-102 were assigned to anomeric carbons of 4-linked β-D-Glu p, 4-linked β-D-xyl p, terminal β-D-Glc p and 3-linked α-L-Rha p.

C-2: The signals at δ 81.97 was assigned to 5-linked α-L-Ara f moiety. Signals for C-2 observed at δ 72.94 and 72.72 were assigned to terminal and 6-linked β-D-Gal p residues, respectively. Signal at δ 72.56 was assigned to 3- and 3,6-linked β-D-Gal p residue. Similarly, C-2 signals assignable to terminal and 6-linked β-D-Glc p were observed at δ 74.81, 74.60 and 73.33, respectively. The C-2 signals in α-L-Rha p residues assignable to terminal, 3-linked and 4-linked were observed at δ 80.02, 76.55 and 70.68, respectively. The signal at δ 81.24 was assigned to 2-linked β-D-Man p residue.

C-3: Signal at δ76.55 was assigned to terminal and 5-linked α-L-Ara f. Signal at δ74.81 was assigned to terminal and 6-linked β-D-Gal p. Further, the signal at δ 81.97 was assigned to 3- and 3,6-linked β-D-Gal p residue. The signals at δ 76.55 and 74.81 were assigned to terminal, 4-linked and 6-linked β-D-Glc p moieties. Similarly, the signals at δ 80.02, 76.55 and 70.6 were assigned to terminal, 3-linked and 4-linked α-L-Rha p moiety, respectively.

C-4: Signal at δ 83.85 was assigned to terminal and 5-linked α-L-Ara f moiety. Signal at δ 70.15 was assigned to terminal β-D-Gal p residue. Signal at δ 70.68 was assigned to 3- and 6-linked β-D-Gal p residue. While the signal at δ 73.33 was assigned to 3,6-linked β-D-Gal p residue. Signals at δ 80.02, 70.68 and 70.15 were assigned to C-4 of 6-linked and terminal β-D-Glc p moiety, respectively. Signals at δ 81-83 were assigned to C-4 of 3-linked, 4-linked and terminal α-L-Rha p moiety.

C-5: Signal due to C-5 of 5-linked α-L-Ara f was observed at δ 69.17 while that of terminal α-L-Ara f was observed at δ 61.25. C-5 signals due to 3-linked, 6-linked and terminal β-D-Gal p residue were observed between δ 74-77, whereas, the C-5 signals due to terminal was observed at δ 75-76 in the case of β-D-Glc p moiety.

C-6: The C-6 signals due to 6- and 3,6-linked β-D-Gal p residues were observed at δ 69.17 whereas 3-linked- and terminal signals were observed at δ 60.93 and 61.25, respectively. Signal due to C-6 in β-D-Glc p residues for terminal was observed between δ 60-62 and the signal at δ 70.1 was observed for 6-linked.

Methyls: The signals observed at δ 16.7, 19.9 and 22.2 were assigned to methyl groups of α-L-Rha p.

The above assignments were further confirmed by carrying out HETCOR experiments.

Amino acids: Signal at δ 16.70 was assigned to Cγ and Cδ methyls of valine, Cβ methyl of alanine and Cδ methyl of methionine. Signal at δ 19.97 was assigned to Cγ methyl of threonine. Signal at δ 22.22 was assigned to Cγ ($CH_2$), Cγ (C—H) of arginine, leucine, isoleucine, lysine and to Cδ and Cε methyls of leucine.

The signal at δ 31.01 was assigned to Cβ ($CH_2$) of arginine, methionine, lysine, proline and Cγ ($CH_2$) of glutamine.

Signal at δ 38.05 was assigned to Cβ ($CH_2$) of asparagine, leucine, phenylalanine, tyrosine, Cα of glycine and Cδ ($CH_2$) of arginine and lysine. Signal at δ 48.45 was assigned to Cα proton of alanine, asparagine, leucine and Cδ of proline.

Signal at δ 59.81 was assigned to Cα protons of arginine, cystine, glutamine, histidine, isoleucine, lysine, methionine, phenylalanine, serine and tyrosine. Signal at δ 60.9 was assigned to Cα proton of valine and threonine while the signal at 61.25 was assigned to Cα proton of proline and Cβ proton of serine.

The signal at δ 68.38 was assigned to Cβ (CH) of threonine.

Signals between δ 108-140 were assigned to the olefinic protons of histidine and aromatic protons of phenylalanine.

Signal at δ 155.64 was assigned to Cε of arginine and C-4 of tyrosine whereas carbonyl signal at δ 166.19 was assigned to glutamine.

In the downfield region, the signals observed between δ 171-175 were assigned to the carbonyl groups of the amino acids alanine, arginine, asparagine, glutamine, glycine, histidine, isoleucine, leucine, lysine, methionine, phenylalanine, proline, serine, threonine and tyrosine.

In conclusion the structure of AGP-HM consists of 6-linked-galactopyranose and 3,6-linked galactopyranose as the backbone and arabinofuranosyl, arabinopyranosyl, rhamnopyranosyl, glucopyranosyl and galactopyranosyl residues in terminal positions. The AGP further contains 3-linked, 4-linked rhamnopyranosyl, 2-linked-mannopyranosyl, 2-linked-glucopyranosyl, 3-linked-, 4-linked galactopyranosyl, 6-linked-, 3,6-linked-glucopyranosyl and 4-linked-xylopyranosyl residues along with methyl uronic acid. The amino acid constituents of the AGP composition were identified as asparagine, glutamine, hydroxyproline, serine, glycine, histidine, arginine, threonine, alanine, proline, tyrosine, valine, methionine, isoleucine, leucine, lysine and phenylalanine. However, sites of attachment of amino acids have not been determined. AGP-LM also possesses similar structure but differs in the molecular weight. Based on the aforesaid data the following structure has been proposed for AGP composition (FIG. 2). Both AGP-HM and AGP-LM possess similar biological activity, hence, AGP composition has been employed for all biological studies.

The Immunological and Pharmacological Properties of the AGP Composition

The cytokine assay, such as IL-2, IFN-γ, IL-10 and other in vivo activities such as delayed type hypersensitivity (DTH) in guinea pigs are described below. A comparison of biological activities of aqueous extract as obtained by the method disclosed in US Application Publication No. 2003/0194456 A1 and AGP composition of the present invention is given in Table-III.

TABLE III

Comparative Biological Efficacy of Aqueous Extract (1) obtained as per the Method disclosed in U.S. application publication No. 2003/0,194,456 A1 and the AGP Composition of the Present Invention (2)

| Sr. No. | Parameters | Aqueous Extract (1) | AGP Composition (2) |
|---|---|---|---|
| 1 | IL-10 induction ($EC_{50}$ in µg/ml) | 2.54 | 1.075 |
| 2 | IL-2 inhibition (% inhibition at 20 ng/ml) | 29.32 ± 5.26 | 51.10 ± 4.33 |
| 3 | IFNγ inhibition (% inhibition at 20 ng/ml) | 33.27 ± 6.52 | 54.50 ± 4.00 |
| 4 | TNFα inhibition (% inhibition at 2 µg/ml) | 44.34 ± 6.64 | 60.68 ± 9.03 |
| 5 | GMCSF inhibition (% inhibition at 200 ng/ml) | 35.57 ± 9.45 | 43.28 ± 6.21 |
| 6 | TPA induced skin hyperplasia ($ED_{50}$ mg/kg) | 36.3 | 2.31 |
| 7 | DTH Model ($ED_{50}$ mg/kg) | 4.34 | 0.58 |
| 8 | MEST ($ED_{50}$ mg/kg) | 14.0 | 6.43 |

Toxicological Studies on the AGP Composition

Acute toxicity ($LD_{50}$) of AGP composition was evaluated in mice and rat by oral and i.v. routes. Group of ten (10) animals from each species per route per dose were medicated and results were calculated on day 15.

The following values were observed for the AGP composition

| | |
|---|---|
| $LD_0$ of mice p.o. | >5000 mg/kg b.wt. |
| $LD_0$ of mice i.v. | >1000 mg/kg b.wt. |
| $LD_0$ of rat p.o. | >5000 mg/kg b.wt. |
| $LD_{50}$ of rat i.v. | >250 mg/kg b.wt. |

Biological Assay of the AGP Composition

Description of the Methods of Evaluation for Human IL-10 Production

In order to evaluate the efficacy of the AGP composition for its therapeutic potential in psoriasis, its role in in vitro IL-10 induction was evaluated by IL-10 production assay with ConA induced PBMCs [Raychudhuri S. P., Farber E. M., Raychudhuri S. K., Int. J. Immunopharmacol., 1999, 21, 609].

Briefly, Human PBMCs (Peripheral blood homonuclear cells) were separated out and stimulated with 10 µg/ml ConA along with various concentrations of AGP composition and incubated for 48 hours at 37° C. in $CO_2$ incubator with 5% $CO_2$. The supernatants were harvested and frozen at −70° C. until quantitation by ELISA. Human IL-10 ELISA kits used were from R and D System for detection of IL-10 in culture supernatant. Percent induction was calculated with reference to control. The results are summarized in Table-IV.

The AGP composition isolated from *Argemone mexicana* exhibited increase in production of IL-10 in ConA activated human PBMCs in the range of 0.0002 µg/ml to 200 µg/ml (FIG. 3). IL-10 was found to be regulatory cytokine in psoriasis treatment and is well known for inducing anti-psoriatic therapy.

IL-10 induction is useful in the treatment and/or prophylaxis of psoriasis, dermatitis, scleroderma, inflammatory disorders and other autoimmune diseases like psoriatic arthritis, plaque psoriasis, guttate psoriasis, rheumatoid arthritis, Crohn's disease, multiple sclerosis, irritable bowel disease, ankylosing spondilitis, systemic lupus erythrometosus, Sjogren's syndrome, allergies like asthma, chronic obstructive pulmonary disease and related conditions such as eczema and scaly itchy patches. IL-10 induction is also useful in other chronic, recurrent and other skin ailments where cutaneous lymphocyte antigen or cutaneous leukocyte antigen is involved.

TABLE IV

Effect of the AGP Composition on IL-10 Induction by ConA induced Human PBMCs

| Concentration of Extract (μg/ml) | Average % Induction |
|---|---|
| 200 | 371.40 |
| 20 | 303.80 |
| 2 | 237.30 |
| 0.2 | 137.20 |
| 0.02 | 114.30 |
| 0.002 | 106.00 |
| 0.0002 | 102.60 |

*The values are depicted in percent increase from basal with reference to control.

Description of the Methods of Evaluation for Human IL-2 and IFN-γ Production

In order to evaluate the efficacy of AGP composition for its therapeutic potential in psoriasis, its role in in vitro IL-2 and IFN-γ modulation was evaluated by IL-2 and IFN-γ production inhibition assay with phytohemagglutin (PHA) induced PBMCs [Brynskov J, Tvede N., *Gut.,* 1990, 31(7), 795].

The aim of this study was to evaluate the effect of AGPs on PHA induced IL-2 and IFN-γ production from human lymphocyte. Briefly, peripheral blood mononuclear cells (PBMC) were obtained from healthy individuals. One million PBMC per ml were stimulated with PHA (5 μg/ml) along with various concentrations of AGP composition isolated from *Argemone mexicana* for 48 hours at 37° C. in $CO_2$ incubator with 5% $CO_2$. The supernatants were harvested and frozen at −70° C. Human IL-2 and Human IFN-γ ELISA kits used were from R and D System for detection of IL-2 and IFN-γ in culture supernatant. Percent inhibition was calculated with reference to control. AGP composition isolated from leaves and/or stems of *Argemone mexicana* was found inhibitory to mitogen induced IL-2 production between 0.002 μg/ml to 20 μg/ml (FIG. 4). This inhibitory activity to mitogen IL-2 production is known to be immunosuppressive and well established to be useful in treatment and/or prophylaxis of psoriasis. The results are summarized in Table-V.

TABLE V

Effect of AGP Composition on IL-2 Production by PHA induced Human PBMCs

| Concentration of AGP Composition(μg/ml) | Average % Inhibition |
|---|---|
| 20.00 | 54.53 |
| 2.00 | 54.49 |
| 0.20 | 53.97 |
| 0.02 | 51.10 |
| 0.002 | 30.56 |
| 0.0002 | 10.87 |
| 0.00002 | 3.75 |

*The values are depicted in percent inhibition with reference to control.

The AGP composition isolated from *Argemone mexicana* was found inhibitory to mitogen induced IFNγ production in the range of 0.0002 μg/ml to 2 μg/ml (FIG. 5). This inhibitory activity to mitogen induced IFN-γ production is known to be immunosuppressive and well established to be useful in treatment and/or prophylaxis of psoriasis. The results are summarized in Table VI.

TABLE VI

Effect of AGP Compositions on IFN-γ Production by PHA induced Human PBMCs

| Concentration of AGP Composition(μg/ml) | Average % Inhibition |
|---|---|
| 20.00 | 55.19 |
| 2.00 | 57.07 |
| 0.20 | 53.69 |
| 0.02 | 54.50 |
| 0.002 | 38.62 |
| 0.0002 | 15.34 |
| 0.00002 | 4.04 |

*The values are depicted in percent inhibition with reference to control.

Description of the Methods of Evaluating for Human GMCSF and TNF-Alpha Production In order to evaluate the efficacy of the AGP compositions of this invention for its therapeutic potential in psoriasis, its role in in vitro granulocyte macrophage colony stimulating factor (GMCSF) and TNF-α modulation was evaluated by GMCSF and TNFγ production inhibition assay with PBMCs stimulated by ConA and LPS.

Briefly, Human PBMCs were separated from blood of healthy volunteers, stimulated with 10 μg/ml ConA along with various concentrations of AGP composition and incubated for 48 hours at 37° C. in $CO_2$ incubator with 5% $CO_2$. 5 μg/ml of LPS was added and incubated for 24 hours under the same conditions. The supernatants were harvested and frozen until quantitation of cytokines using ELISA. Percent inhibition was calculated with reference to control.

The AGP composition isolated from *Argemone mexicana* was found inhibitory to mitogen induced GMCSF production in range of 0.02 μg/ml to 2 μg/ml (FIG. 6). This inhibitory activity to mitogen induced GMCSF production is known to be immunosuppressive and well established to be useful in treatment and/or prophylaxis of psoriasis. The results are summarized in Table-VIII.

TABLE VII

Effect of AGP Composition on GMCSF Production by ConA and LPS induced Human PBMCs

| Concentration of AGP Composition(μg/ml) | Average % Inhibition |
|---|---|
| 2.00 | 32.31 |
| 0.20 | 43.28 |
| 0.02 | 35.41 |

*The values are depicted in percent inhibition with reference to control.

AGP composition isolated from *Argemone mexicana* was found inhibitory to mitogen induced TNF-α production in range of 0.002 μg/ml to 2 μg/ml (FIG. 7). This inhibitory activity to mitogen TNF-α production is known to be immunosuppressive and well established to be useful in treatment and/or prophylaxis of psoriasis. The results are summarized in Table VIII.

TABLE VIII

Effect of AGP Compositions on TNF-α production by ConA and LPS induced Human PBMCs

| Concentration of AGP composition(μg/ml) | Average % Inhibition |
|---|---|
| 2.00 | 60.68 |
| 0.20 | 46.18 |
| 0.02 | 22.02 |
| 0.002 | 10.30 |

*The values are depicted in percent inhibition with reference to control.

Effect of the AGP Composition on NGF Induced Human Keratinocytes Proliferation Keratinocytes were purchased from GIBCO (USA) and were maintained in Keratinocyte-serum free medium (GIBCO, # 10744-019) supplemented with growth factors. Approximately, 150 μl of KGM (keratinocyte growth medium) containing 2000 cells were added in each well of 96 well flat bottom plate. Next day medium was changed with 1:2 volume of KGM:KBM (keratinocyte basal medium). Thirty microliters of diluted AGP composition was added in each well in triplicate except cell control wells. NGF (Nerve growth factor) 100 ng/ml was added in each well. Medium was removed after 8 days of incubation. Cells were rinsed with PBS. LDH (Lactate dehydrogenase) development lysis solution was added and incubated for 10 min at 37° C. OD was measured in ELISA reader at wavelength of 492 nm. Percent proliferation/inhibition was calculated. The results are summarized in Table-IX

TABLE IX

Effect of AGP Composition on NGF Induced Human Keratinocytes Proliferation

| AGP Composition (μg/ml) | Average % Inhibition |
|---|---|
| 40.00 | 79.15 |
| 8.00 | 74.53 |
| 1.60 | 71.49 |
| 0.32 | 66.78 |
| 0.064 | 55.75 |
| 0.0128 | 26.78 |
| 0.0025 | 15.36 |
| 0.0005 | 6.18 |
| 0.0001 | 3.03 |

*The values are depicted in percent inhibition with reference to control.

The AGP composition isolated from *Argemone mexicana* was found inhibitory to NGF induced human keratinocytes proliferation in range of 0.0001 μg/ml to 40 μg/ml (FIGS. 8 & 9). This inhibitory activity to NGF induced human keratinocytes proliferation is known to be immunosuppressive and well established to be useful in treatment and/or prophylaxis of psoriasis.

Description of the Methods of Evaluation of In Vivo Immunosuppression Using Delayed Type Hypersensitivity in Guinea Pigs This standard procedure was used for evaluation of the in vivo efficacy of AGP composition for its ability to inhibit Purified protein derivative (PPD) induced delayed type hypersensitivity in guinea pigs. Briefly, guinea pigs were sensitized with 100 μg of PPD intradermally with Freund's complete adjuvant. Two subsequent boosters of 100 μg of PPD with Freund's incomplete adjuvant were given at a week interval. AGP composition was administered orally once a day for 28 days. The animals were challenged with 100 μg of PPD intradermally on $28^{th}$ day and the difference in the control and PPD injected skin thickness was measured after 24 hours post challenge with a Varnier's caliper. The differences of skin thickness were calculated by subtracting saline injected skin thickness in same guinea pigs. Percent inhibition was calculated with reference to saline sensitized animals.

The AGP composition isolated from *Argemone mexicana* was found to be immunosuppressive to PPD sensitized and PPD challenged guinea pigs in the range of 20-65.89% inhibition at the dose of 0.10-100 mg/kg p.o. Effective dose causing 50% inhibition ($ED_{50}$) of skin thickness in PPD challenged guinea pigs was found to be 0.508 mg/kg p.o (FIG. 10). The potent immunosuppressive property is well established and is beneficial for anti-psoriasis treatment.

Immunosuppression in DTH model is a useful model for several diseases where immunosuppression is required, such as psoriasis, dermatitis, scleroderma, inflammatory disorders and other autoimmune diseases like psoriatic arthritis, plaque psoriasis and guttate psoriasis. The results are summarized in Table-X.

TABLE X

Effect of the AGP composition on skin thickness in guine pigs challenged with PPD

| Concentration of AGP Composition mg/kg | Percent Response |
|---|---|
| 0.01 | 0.000 |
| 0.10 | 20.000 |
| 1.00 | 62.680 |
| 10.00 | 67.930 |
| 30.00 | 61.510 |
| 100.00 | 65.880 |

Description of the Methods of Evaluation of TPA

Balb/C mice were randomized and acclimatized in cages 5 days before the experiment. Hair were removed by using Anne French topical application and cleaned properly. Groups were made consisting of six mice in each. Acetone control group and TPA (12-O-tetradecanoylphorbol-13-acetate) control groups were taken along with the test drug group. AGP composition was dissolved in the recommended vehicle (acetone) and animals were dosed orally for 4 days once daily. Twenty microliter of 100 nM TPA was applied on the second day onto the cleaned skin surface and allowed to be absorbed. Animals were sacrificed 72 hours after TPA application. The skin pieces were fixed in 10% formalin for 3 days. Histopathological slides were made by following standard methods. Epidermal thickness was measured in at least 10 different areas by using a oculometer and results were expressed in percent inhibition (FIG. 11). The results are summarized in Table-XI.

TABLE XI

Effect of the AGP Composition on TPA Model

| Groups | Dose (mg/kg, p.o.) | Increase in Epidermal Thickness (μm) | % Inhibition |
|---|---|---|---|
| Acetone control group | — | 23.08 | — |
| TPA control group | — | 52.88 | 0.00 |
| AGP Composition | 30.00 | 25.38 | 92.30 |
|  | 10.00 | 29.67 | 77.89 |
|  | 3.00 | 35.63 | 57.90 |
|  | 1.00 | 50.08 | 9.37 |
|  | 0.30 | 52.63 | 0.84 |
|  | 0.10 | 52.67 | 0.70 |

*The values are depicted in percent inhibition with reference to TPA control group.

Description of the Methods of Evaluation of In Vivo Immunosuppression Using Mouse Ear Swelling Test (MEST)

This standard procedure was used for evaluation of the in vivo efficacy of AGP compositions for their ability to inhibit DNFB induced delayed type hypersensitivity in mice [Cornacoff J. B, House R. V, Dean J. H., *Fundam. Appl. Toxicol.*, 1988, 10(1), 40; Fundam. Appl. Toxicol., 1992, 19(1), 157].

Briefly, C57BL6 mice were used for the test. Mice were sensitized with 0.2% DNFB (in 1:4 of Olive oil and Acetone) on back of the mice. Three boosters DNFB application were done every third day. The mice were challenged with 0.2% DNFB (in 1:4 of Olive oil and Acetone) on ear pinna. Ear thickness in the center of the ear was measured after 24 hours with the help of Varnier caliper. The analysis was performed, by calculating percent inhibition with respect to a negative control were given orally at different doses. The results are summarized in Table-XII.

TABLE XII

Effect of AGP Composition on DNFB induced Mice Ear Swelling Test in Female C57/BL6 Mice

| Sr. No. | Treatment | Percent Inhibition |
|---|---|---|
| 1 | Milli Q water 10 ml/kg, p.o. Negative control for AGP composition | 0.00 |
| 2 | 2% Tween 80, 10 ml/kg, p.o. Negative control for Cyclosporin | 0.00 |
| 3 | AGP Composition - 0.1 mg/kg, p.o. | 0.00 |
| 4 | AGP Composition - 1 mg/kg, p.o. | 18.00 |
| 5 | AGP Composition - 3 mg/kg, p.o. | 33.05 |
| 6 | AGP Composition - 10 mg/kg, p.o. | 43.62 |
| 7 | AGP Composition - 30 mg/kg, p.o. | 58.52 |
| 8 | AGP Composition - 100 mg/kg, p.o. | 69.51 |
| 9 | Cyclosporine 25 mg/kg, p.o. | 65.16 |

Data represented as percent inhibition with each from 7-12 animals. The AGP composition was compared with Milli Q water treated group and cyclosporine was compared with animals treated with 2% Tween 80

The AGP composition from the leaves and/or stem of *Argemone mexicana* were found to be immunosuppressive to DNFB sensitized C57BL6 mice. The $ED_{50}$ for AGP composition was determined to be 6.43 mg/kg (FIG. 12). The potent immunosuppressive property is well established and beneficial for treatment or prophylaxis of psoriasis.

Immunosuppression in the MEST model is useful in evaluating effect for several diseases where immunosuppression is required, such as psoriasis, dermatitis, scleroderma, inflammatory disorders and other autoimmune diseases like psoriatic arthritis, plaque psoriasis, guttate psoriasis, rheumatoid arthritis, Crohn's disease, multiple sclerosis, ankylosing spondilitis, systemic lupus erythrometosus, Sjogren's syndrome, allergies like asthma, chronic obstructive pulmonary disease and related conditions as eczema, scaly itchy patches.

The invention is further illustrated by the following non-limiting examples.

EXAMPLE 1

Isolation of AGP Composition, AGP-HM and AGP-LM

10 Kg fresh leaves of *Argemone mexicana* were ground and extracted with demineralised water (15 liters). The slurry was centrifuged and the aqueous extract was concentrated below 40° C. under vaccum. The concentrated material was lyophilized to give 0.54 Kg of dry solid.

500 g of the dry aqueous extract was dissolved in 6 liters of water, centrifuged and decanted. The supernatant was loaded on a cation exchange column (5 liters) at the rate of 10 ml/min. The eluate (7.5 liters) was collected, concentrated (2.5 liters) and loaded on an anion exchange column (5 liters). The eluate (3 liters) was concentrated to approximately 1.5 liters. The experiment was repeated with another 0.5 kg of the material (aqueous extract).

The combined eluates (1.5 liters) each were mixed and concentrated to 2.5 liters and loaded on a cation exchange column. The eluate (3 liters) was concentrated up to 1.2 liters and loaded on an anion exchange column. The eluate (1.5 liters) was lyophilized to give 42.39 g of a powder.

42 g of the above powder was dissolved in 600 ml of water and partitioned between n-butanol (3×400 ml) and water. The n-butanol layer was discarded. 3 liters of methanol was poured in to the aqueous layer (600 ml) when a solid precipitated out. The solution was centrifuged and the supernatant decanted. The supernatant was concentrated to a volume of ca. 300 ml. Methanol (1 liter) was poured again to precipitate the methanol insolubles. The solution was centrifuged and the supernatant decanted. The precipitated solid from both experiments were lyophilized (8.75 g). The dry materials were dissolved in water, and subjected to XAD-2® (polystyrene polymeric absorbent) column, twice. The water eluate was lyophilized to give 6.10 g of AGP composition. This was further subjected to sephacryl chromatography to yield 5 mg of AGP-HM and 10.3 mg of AGP-LM.

EXAMPLE 2

Isolation of AGP Composition, AGP-HM and AGP-LM

22 Kg of fresh leaves of *Argemone mexicana* were ground and extracted with demineralised water (36 liters). The slurry was centrifuged and the aqueous extract was concentrated below 40° C. under vaccum. The concentrated material was lyophilized to give 1.25 Kg of dry solid.

1.2 kg of the dry aqueous extract was dissolved in 12 liters of water, centrifuged and decanted. The supernatant was loaded on a cation exchange column (5 liters) at the rate of 10 ml/min. The eluate (15.5 liters) was collected, concentrated (5.5 liters) and loaded on an anion exchange column (5 liters). The eluate (6.25 liters) was concentrated to approximately 3.2 liters.

The eluate (3.2 liters) was concentrated to 2.6 liters and loaded on a cation exchange column. The eluate (4 liters) was concentrated up to 1.5 liters and loaded on an anion exchange column. The eluate (1.6 liters) was lyophilized to give 54 g of a powder.

40 g of the above powder was dissolved in 700 ml of water and partitioned between n-butanol (3×500 ml) and water. The n-butanol layer was discarded. 4 liters of methanol was poured in to the aqueous layer (675 ml) when a solid precipitated out. The solution was centrifuged and the supernatant decanted. The supernatant was concentrated to 400 ml. Methanol (3 liter) was poured again to precipitate the methanol insolubles. The solution was centrifuged and the supernatant decanted. The precipitated solids were lyophilized (7.3 g). The dry material thus obtained was dissolved in water, and subjected to XAD-2® (polystyrene polymeric absorbent) column, twice. The water eluate was lyophilized to give 5.5 g of AGP composition. This was further subjected to sephacryl chromatography to yield 4.5 mg of AGP-HM 12.4 mg of AGP-LM.

EXAMPLE 3

TABLE XIII

Unit Formulae for a Capsule Formulation Comprising the AGP of the Present Invention and Pharmaceutically Acceptable Carriers

| Sr. No. | Ingredient | Strength (mg/capsule) | |
|---|---|---|---|
| 01 | AGP | 50 | 200 |
| 02 | Microcrystalline Cellulose USNF (Avicel PH 102) | 39 | 39 |
| 03 | Croscarmellose Sodium USNF (Ac-Di-SOL) | 10 | 10 |
| 04 | Colloidal Silicon Dioxide USNF (Aerosil 200) | 0.5 | 0.5 |
| 05 | Magnesium Stearate USNF | 0.5 | 0.5 |
| | Total | 100 | 250 |
| 06 | Hard gelatin capsule | 1 (size '2' with orange body and orange cap) | 1 (size '00' with orange body and red cap) |

The abovementioned ingredients given in Table-XIII can be blended until uniform and then filled in hard gelatin capsules of the size "00". The processing area is ideally maintained at 40±5% RH at 18-22° C.

A typical process for preparation of the composition of the invention is illustrated below:

The active ingredient, Microcrystalline Cellulose, Croscarmellose Sodium, Magnesium Stearate and colloidal silicon dioxide are blended until uniform. They are filled in hard gelatin capsules of size "00". The processing area is ideally maintained at 40±5% RH at 18° C. to 22° C.

When a topical application is administered, the amount of the of *Argemone mexicana* plant ranges from 0.1% to 10% by weight of the extract.

A Unit Formuale for an ointment for topical application comprising the AGP and carriers is summarized in Table-XIV.

TABLE XIV

Unit Formulae for an Ointment for Topical Application Comprising the AGP of the Present Invention and Pharmaceutically Acceptable Carriers

| Sr. No. | Ingredient | Amount |
|---|---|---|
| 01 | AGP | 1.0 gm |
| 02 | Water | 100 ml |
| 03 | Hydroxypropyl Methyl Cellulose | 4.0 gm |

A typical process for preparation of the ointment for topical application comprised slow blending of the all the ingredients to a smooth gel by conventional methods and filling into tubes.

The invention claimed is:

1. A composition containing Arabinogalactan-Protein (AGP), the AGP having an average molecular weight range between 10 KD to 150 KD, obtained by a process comprising the steps of:
   i) extracting 1 part by weight of the leaves, stems or both of *Argemone Mexicana* plant with 1 to 10 parts by weight of water, a $C_{1-3}$ alcohol or mixtures thereof to obtain an extract and optionally partially or completely concentrating or lyophilizing the extract;
   ii) subjecting the extract, partially concentrated extract or an aqueous solution of the completely concentrated or lyophilized extract as obtained in step i) to anion exchange chromatography followed by cation exchange chromatography or cation exchange chromatography followed by anion exchange chromatography to obtain a neutral extract;
   iii) fractionating the neutral extract obtained in step ii) with n-butanol and separating the aqueous phase and the n-butanol phase, fractionating the separated aqueous phase with n-butanol and separating the aqueous phase and n-butanol phase; and
   iv) mixing and agitating the aqueous phases obtained in step iii) with methanol or ethanol, and isolating precipitated solids to obtain a methanol or ethanol insoluble fraction which contains said AGP.

2. The composition according to claim 1, wherein in step i) the $C_{1-3}$ alcohol is selected from methanol, ethanol, 1-propanol and 2-propanol.

3. The composition according to claim 2, wherein the $C_{1-3}$ alcohol is ethanol.

4. The composition according to claim 1, wherein the cation exchange chromatography is carried out over sulphonated polystyrene strong-acid cation exchangers or carboxylic acid-type weak acid cation exchangers.

5. The composition according to claim 1, wherein the anion exchange chromatography is carried out over aliphatic amine-type weak base anion exchangers or strong base anion exchangers.

6. The composition according to claim 1 wherein, the AGP comprises 6-linked galactopyranose and 3,6-linked galactopyranose as the back-bone and arabinofuranosyl, arabinopyranosyl, rhamnopyranosyl, glucopyranosyl and galactopyranosyl residues in terminal positions, and 3-linked-4-linked rhamnopyranosyl, 2-linked-mannopyranosyl, 2-linked-glucopyranosyl, 3-linked, 4-linked galactopyranosyl, 6-linked, 3,6-linked-glucopyranosyl, 4-linked-xylopyranosyl residues and methyl uronic acid.

7. The composition according to claim 1 wherein, the AGP is 45-9 8% by weight of carbohydrates.

8. The composition according to claim 1 wherein, the AGP is 2-20% by weight of proteins.

9. A method for isolating Arabinogalactan-Protein (AGP) composition, comprising the steps of:
   i) extracting 1 part by weight of the leaves, stems or both of *Argemone Mexicana* plant with 1 to 10 parts by weight of water, a $C_{1-3}$ alcohol or mixtures thereof to obtain an extract and optionally partially or completely concentrating or lyophilizing the extract;
   ii) subjecting the extract, partially concentrated extract or an aqueous solution of the completely concentrated or lyophilized extract as obtained in step i) to anion exchange chromatography followed by cation exchange chromatography or cation exchange chromatography followed by anion exchange chromatography to obtain a neutral extract;
   iii) fractionating the neutral extract obtained in step ii) with n-butanol and separating the aqueous phase and the n-butanol phase, fractionating the separated aqueous phase with n-butanol and separating the aqueous phase and n-butanol phase;
   iv) mixing and agitating the aqueous phases obtained in step iii) with methanol or ethanol, and isolating precipitated solids to obtain a methanol or ethanol insoluble fraction; and
   v) subjecting the insoluble fraction obtained in step iv) to successive gel chromatography and size exclusion chromatography to obtain the Arabinogalactan-Protein (AGP) composition.

10. The method according to claim 9, wherein the $C_{1-3}$ alcohol is selected from methanol, ethanol, 1-propanol or 2-propanol.

11. The method according to claim 10, wherein the $C_{1-3}$ alcohol is ethanol.

12. The method according to claim 9, wherein the cation exchange chromatography is carried out over sulphonated polystyrene strong-acid cation exchangers or carboxylic acid-type weak acid cation exchangers.

13. The method according to claim 9, wherein the anion exchange chromatography is carried out over aliphatic amine-type weak base anion exchangers or strong base anion exchangers.

14. The method according to claim 9, wherein the gel chromatography is carried out over a polymeric adsorbent.

15. The method for isolation of purified Arabinogalactan-Protein (AGP) composition, according to claim 9, wherein the size exclusion chromatography is carried out over sephacryl.

16. A method for isolation of purified Arabinogalactan-Protein (AGP) comprising the steps of:
   i) extracting 1 part by weight of the leaves, stems or both of *Argemone Mexicana* plant with 1 to 10 parts by weight of water, a $C_{1-3}$ alcohol or mixtures thereof to obtain an extract and optionally partially or completely concentrating or lyophilizing the extract;
   ii) subjecting the extract, partially concentrated extract or an aqueous solution of the completely concentrated or lyophilized extract as obtained in step i) to anion exchange chromatography followed by cation exchange chromatography or cation exchange chromatography followed by anion exchange chromatography to obtain a neutral extract;
   iii) fractionating the neutral extract obtained in step ii) with n-butanol and separating the aqueous phase and the n-butanol phase, fractionating the separated aqueous phase with n-butanol and separating the aqueous phase and n-butanol phase;
   iv) mixing and agitating the aqueous phases obtained in step iii) with methanol or ethanol, and isolating precipitated solids to obtain a methanol or ethanol insoluble fraction; and
   v) subjecting the insoluble fraction obtained in step iv) to successive gel chromatography and size exclusion chromatography to obtain the Arabinogalactan-Protein (AGP) composition;
      wherein the gel chromatography is carried out over a polymeric adsorbent selected from a polystyrene or acrylic ester polymeric adsorbent.

17. The method according to claim 16, wherein the size exclusion chromatography is carried out over sephacryl selected from sephacryl S-100, sephacryl S-200 HR, and sephacryl S-300 HR.

18. A pharmaceutical composition comprising a therapeutically effective amount of the Arabinogalactan-Protein (AGP) composition of claim 1 and a pharmaceutically acceptable excipient.

19. The composition according to claim 18, further comprising at least one of non-toxic compatible fillers, binders, disintegrants, buffers, preservatives, antioxidants, lubricants, and flavouring agents.

20. The composition, according to claim 18, wherein the pharmaceutically acceptable excipient is selected from sugars, starches, cellulose and its derivatives calcium phosphates; sodium sulphate; calcium sulphate; polyvinylpyrrolidone; polyvinyl alcohol; stearic acid; vegetable oils; nonionic, cationic and anionic surfactants; ethylene glycol polymers; β-cyclodextrin; fatty alcohols; hydrolyzed cereal solids or mixtures thereof.

* * * * *